United States Patent [19]

Senger et al.

[11] Patent Number: 6,022,541

[45] Date of Patent: *Feb. 8, 2000

[54] IMMUNOLOGICAL PREPARATION FOR CONCURRENT SPECIFIC BINDING TO SPATIALLY EXPOSED REGIONS OF VASCULAR PERMEABILITY FACTOR BOUND IN-VIVO TO A TUMOR ASSOCIATED BLOOD VESSEL

[75] Inventors: Donald R. Senger, Medfield; Harold F. Dvorak, Newton, both of Mass.

[73] Assignee: Beth Israel Deaconess Medical Center, Boston, Mass.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/807,992

[22] Filed: Mar. 3, 1997

Related U.S. Application Data

[63] Continuation-in-part of application No. 08/327,709, Oct. 24, 1994, Pat. No. 5,659,013, which is a continuation of application No. 07/779,384, Oct. 18, 1991, abandoned.

[51] Int. Cl.[7] ........................ A61K 39/395; A61K 49/00; C12P 21/08; C07K 16/18

[52] U.S. Cl. ........................ 424/172.1; 424/1.49; 424/9.1; 424/182.1; 424/178.1; 424/133.1; 424/174.1; 530/387.3; 530/388.2; 530/389.1; 530/391.3; 530/391.7

[58] Field of Search ........................ 424/1.49, 9.1, 424/172.1, 182.1, 178.1, 174.1, 133.1; 530/388.2, 391.3, 391.7, 387.3, 389.1

[56] References Cited

U.S. PATENT DOCUMENTS

| 4,514,505 | 4/1985 | Canfield et al. ........................ 436/500 |
| 5,659,013 | 8/1997 | Senger et al. ........................ 530/350 |

OTHER PUBLICATIONS

Asano, M et al. Hybridoma. 14(5):475–480, Oct. 1995.
De Santes, K et al. Cancer Research. 52:1916–1923, Apr. 1, 1992.

*Primary Examiner*—David Saunders
*Assistant Examiner*—F. Pierre VanderVegt
*Attorney, Agent, or Firm*—David Prashker

[57] ABSTRACT

The present invention provides an immunological preparation comprising not less than two types of conjugate molecules in admixture for concurrent specific binding to a spatially exposed region of vascular permeability factor (VPF) bound in-vivo to a tumor-associated blood vessel. Each conjugate molecule type comprises at least a binding portion of an antibody specific for an epitope present within a spatially exposed region of bound VPF; and an effector moiety covalently bound to the specific binding portion. The immunological preparation has wide uses and applications including analytical studies, in-vivo diagnostic testing, and in-vivo therapeutic treatments.

5 Claims, 10 Drawing Sheets

| | | |
|---|---|---|
| VEGF₁₂₁ | -26 | MNFLLSWVHWSLALLLYLHHAKWSQAAPMAEGGGQNHHEVVKFMDVYQRS |
| VEGF₁₆₅ | -26 | MNFLLSWVHWSLALLLYLHHAKWSQAAPMAEGGGQNHHEVVKFMDVYQRS |
| VEGF₁₈₉ | -26 | MNFLLSWVHWSLALLLYLHHAKWSQAAPMAEGGGQNHHEVVKFMDVYQRS |
| VEGF₂₀₆ | -26 | MNFLLSWVHWSLALLLYLHHAKWSQAAPMAEGGGQNHHEVVKFMDVYQRS |
| VEGF₁₂₁ | 25 | YCHPIETLVDIFQEYPDEIEYIFKPSCVPLMRCGGCCNDEGLECVPTEES |
| VEGF₁₆₅ | 25 | YCHPIETLVDIFQEYPDEIEYIFKPSCVPLMRCGGCCNDEGLECVPTEES |
| VEGF₁₈₉ | 25 | YCHPIETLVDIFQEYPDEIEYIFKPSCVPLMRCGGCCNDEGLECVPTEES |
| VEGF₂₀₆ | 25 | YCHPIETLVDIFQEYPDEIEYIFKPSCVPLMRCGGCCNDEGLECVPTEES |
| VEGF₁₂₁ | 75 | WITMQIMRIKPHQGQHIGEMSFLQHNKCECRPPKDRARGEK--------- |
| VEGF₁₆₅ | 75 | WITMQIMRIKPHQGQHIGEMSFLQHNKCECRPPKDRARGEK--------- |
| VEGF₁₈₉ | 75 | WITMQIMRIKPHQGQHIGEMSFLQHNKCECRPKKDRARGEKKSVRGKGGR |
| VEGF₂₀₄ | 75 | WITMQIMRIKPHQGQHIGEMSFLQHNKCECRPKKDRARGEKKSVRGKGGR |

FIG. 1A

```
VEGF₁₂₁  ------------------------------------------------------ -PCGPCSERRKHLFVQDPQ
VEGF₁₆₅  -------------------- PCGPCSERRKHLFVQDPQ
VEGF₁₈₉  125 QKRKRKKSRYKSWSV---------------------------------
VEGF₂₀₄  125 QKRKRKKSRYKSWSVYVGARCCLMPWSLPGPHPCGPCSERRKHLFVQDPQ

VEGF₁₂₁  --------------------- CDKPRR
VEGF₁₆₅  ---------------------
VEGF₁₈₉  134 TCKCSCKNTDSRCKAROLELNERTCRCDKPRR
VEGF₂₀₄  158 TCKCSCKNTDSRCKAROLELNERTCRCDKPRR
        175 TCKCSCKNTDSRCKAROLELNERTCRCDKPRR
```

FIG. 1B

IMMUNOLOGICAL PREPARATION FOR CONCURRENT SPECIFIC BINDING TO SPATIALLY EXPOSED REGIONS OF VASCULAR PERMEABILITY FACTOR BOUND IN-VIVO TO A TUMOR ASSOCIATED BLOOD VESSEL

CROSS REFERENCE

This application is a Continuation-In-Part of U.S. patent application Ser. No. 08/327,709 filed Oct. 24, 1994, now U.S. Pat. No. 5,659,013 issued Aug. 19, 1999; which was a Continuation of U.S. patent application Ser. No. 07/779,384 filed Oct. 18, 1991, now abandoned.

FIELD OF THE INVENTION

The present invention is concerned generally with vascular permeability factor bound in-vivo to tumor-associated blood vessels; and is directed particularly to an immunological admixture comprising not less than two types of antibody-effector conjugate molecules, each of which is able to bind concurrently to the same or different spatially exposed regions of vascular permeability factor bound in-vivo.

BACKGROUND OF THE INVENTION

Vascular permeability factor (hereinafter "VPF") is a 34–43 kilodalton glycoprotein and is a potent inducer of microvascular hyperpermeability. As such, VPF is believed to be responsible for the vascular hyperpermeability and consequent plasma protein-rich fluid accumulation that occurs in-vivo with solid tumors and ascites tumors [Senger et al., *Science* 219: 983–985 (1983); Dvorak et al., *J. Immunol.* 122: 166 (1979); Nagy et al., *Biochim. Biophys. Acta.* 948: 305 (1988); Senger et al., *Federation Proceedings* 46: 2102 (1987)]. On a molar basis, VPF increases microvascular permeability with a potency which is typically 50,000 times that of histamine [Senger et al., *Cancer Res.* 50: 1774–1778 (1990)].

VPF is also known as vascular endothelial growth factor (or "VEGF") because of its mitogenic effects on vascular endothelial cells (hereinafter "EC"). VPF is a specific EC mitogen and stimulates endothelial cell growth and angiogenesis [Conn et al., *Proc. Natl. Acad. Sci. USA* 87: 2628–2632 (1990); Ferrara et al., *Biochem. Biophys. Res. Comm.* 161: 851–858 (1989); Gospodarowicz et al., *Proc. Natl. Acad. Sci. USA* 86: 7311–7315 (1989); Keck et al., *Science* 246: 1309 (1989); Leung et al., *Science* 246: 1306 (1989); Connolly et al., *J. Clin. Invest.* 84: 1470–1478 (1989)]. In addition, VPF also exerts a number of other effects on endothelial cells in-vivo. These include: an increase in intracellular calcium; a stimulation of inositol triphosphate formation; a provocation of von Willebrand factor release; and a stimulation of tissue factor expression [Brock et al., *Am. J. Pathol.* 138: 213 (1991); Clauss et al., *J. Exp. Med.* 172: 1535 (1990)].

VPF is typically synthesized and secreted in-vivo by a variety of cultured tumor cells, transplantable animal tumors, and many different primary and metastatic human tumors [Dvorak et al., *J. Exp. Med.* 174: 1275–1278 (1991); Senger et al., *Cancer Res.* 46: 5629–5632 (1986); Plate et al., *Nature* 359: 845–848 (1992); Brown et al., *Am. J. Pathol.* 143: 1255–1262 (1993)]. Solid tumors must generate a vascular stroma in order to grow beyond a minimal size [Folkman, J. and Y. Shing, *J. Biol. Chem.* 267: 10931–10934 (1992)]. In addition, it has been found that some normal embryonic and normal adult tissues express mRNA for VPF synthesis [Phillips et al., *Endocrinology* 127: 965–967 (1991); Berse et al., *Mol. Biol. Cell.* 3: 211–220 (1992); Breier et al., *Development* 114: 521–532 (1992)]. VPF also has been reported to induce monocyte procoagulant activity and cell migration [Clauss et al., *J. EX. Med.* 172: 1535–1545 (1990)]. For these reasons, VPF today is believed able to induce angiogenesis generally and tumor stroma formation particularly in two ways: directly, as an endothelial cell growth factor; and, indirectly, by causing leakage of plasma proteins including fibrinogen (which clots to form an extravascular fibrin gel matrix and stimulates neovascularization with the subsequent deposition of mature connective tissue stroma). Consistent with this mechanism of action, monoclonal antibody against VPF has been shown to suppress growth and decrease the density of blood vessels in experimental tumors [Kim et al., *Nature* 362: 841–844 (1993)].

Structurally and chemically, VPF is a dimeric protein which is produced in-vivo in at least four major variant forms as a result of alternative splicing of mRNA [Houck et al., *Mol. Endocrinol.* 5: 1806–1814 (1991); Keck et al., *Science* 246: 1309–1312 (1989); Leung et al., *Science* 246: 1306–1309 (1989); Tischer et al., *Biochem. Biophys. Res. Commun.* 165: 1198–1206 (1989)]. In addition, complimentary DNAs coding for VPF obtained from human, bovine, rat, and guinea pig sources have been cloned [Berse et al., *Mol. Biol. Cell.* 3: 211–220 (1992); Conn et al., *Proc. Natl. Acad. Sci. USA* 87: 2628–2632 (1990)].

Under in-vivo conditions, the events induced by VPF apparently result from a direct interaction between the intact VPF molecule and specific endothelial cell surface receptors, two of which (flt-1 and kdr) have recently been identified [deVries et al., *Science* 255: 989–991 (1992); Terman et al., *Biochem. Biophys. Res. Commun.* 187: 1579–1586 (1992)]. Investigation of VPF and its receptors in tumors and vasculature remains an area of primary interest [Brown et al., *Cancer Res.* 53: 4727–4735 (1993); Brown et al., *Am. J. Pathol.* 143: 1255–1262 (1993)].

It will be noted and appreciated also that many research investigations reported in the scientific literature have employed antibodies raised against VPF in order to identify and characterize the functions, properties, and attributes of the VPF molecule in-vivo. Merely illustrating the range and variety of these investigations and published reports are the following: Preparation of antibodies [U.S. Pat. No. 5,036, 003]; monoclonal antibodies to suppress growth and decrease density of blood vessels in tumors [Kim et al., *Nature* 362: 841–844 (1993)]; inhibition of tumor growth and metastasis by antibody to VPF [Asano et al., *Cancer Res.* 55: 5296–5301 (1995)]; inhibition of VPF activity with specific antibodies [Sioussat et al., *Arch. Biochem. Biophys.* 301: 15–20 (1993)]; the structure of solid tumors and their vasculature [Dvorak et al., *Cancer Cells* 3: 77–85 (1991)]; and the distribution of VPF in tumors and the concentration of VPF in tumor blood vessels (Dvorak et al., *J. Exp. Med.* 174: 1275–1278 (1991)]. The text of each of these publications is expressly incorporated by reference herein.

Despite the ever-increasing body of knowledge regarding VPF, its functions, and its role in tumor angiogenesis, no meaningful or substantial information regarding the use and preparation of specific anti-VPF antibodies as markers of bound VPF in-vivo existed prior to 1991; and no diagnostic or therapeutic molecule specific for VPF bound in-vivo to tumor associated blood vessels existed prior to applicants' parent invention comprising antibody-effector conjugated compounds targeting bound VPF which is the subject matter of U.S. patent application Ser. No. 779,384 filed Oct. 18, 1991 as well as the presently continuing applications U.S. Ser. No. 327,709 filed Oct. 24, 1994 and U.S. Ser. No. 464,956 filed Jun. 5, 1996. Thus, the development of additional improvements comprising anti-VPF conjugated molecules prepared as an admixture of different types and having the specific capability to bind to one or more spatially exposed regions of VPF bound in-vivo will be recognized as a major advance and unexpected improvement in this field.

SUMMARY OF THE INVENTION

The present invention has multiple aspects and formats. A first aspect provides an immunological preparation for concurrent specific binding to spatially exposed regions of vascular permeability factor (VPF) bound in-vivo to a tumor-associated blood vessel, said immunological preparation comprising not less than two types of conjugate molecules in admixture, (a) wherein a first type of conjugate molecule comprises
   at least a binding portion of a first antibody specific for an epitope presented by one of the spatially exposed regions of VPF after being bound in-vivo, and
   an effector moiety covalently bound to said first antibody; and (b) wherein a second type of conjugate molecule comprise
   at least a binding portion of a second antibody specific for an epitope presented by another of the spatially exposed regions of VPF after being bound in-vivo, and
   an effector moiety covalently bound to said second antibody.

Another aspect of the invention provides an immunological preparation for concurrent specific binding to a spatially exposed region of vascular permeability factor (VPF) bound in-vivo to a tumor-associated blood vessel, said immunological preparation comprising not less than two types of conjugate molecules in admixture, (a) wherein a first type of conjugate molecule comprises
   at least a binding portion of an antibody specific for an epitope presented by a spatially exposed region of VPF after being bound in-vivo, and
   a first type of effector moiety covalently bound to said antibody; and (b) wherein a second type of conjugate molecule comprises
   at least a binding portion of an antibody specific for an epitope presented by a spatially exposed region of VPF after being bound in-vivo, and
   a second type of effector moiety covalently bound to said antibody.

BRIEF DESCRIPTION OF THE FIGURES

The present invention may be more easily understood and better appreciated when taken in conjunction with the accompanying drawing, in which:

FIG. 1 is a statement of the amino acid sequence for the four major variant forms of VPF;

DETAILED DESCRIPTION OF THE INVENTION

Figure 2:
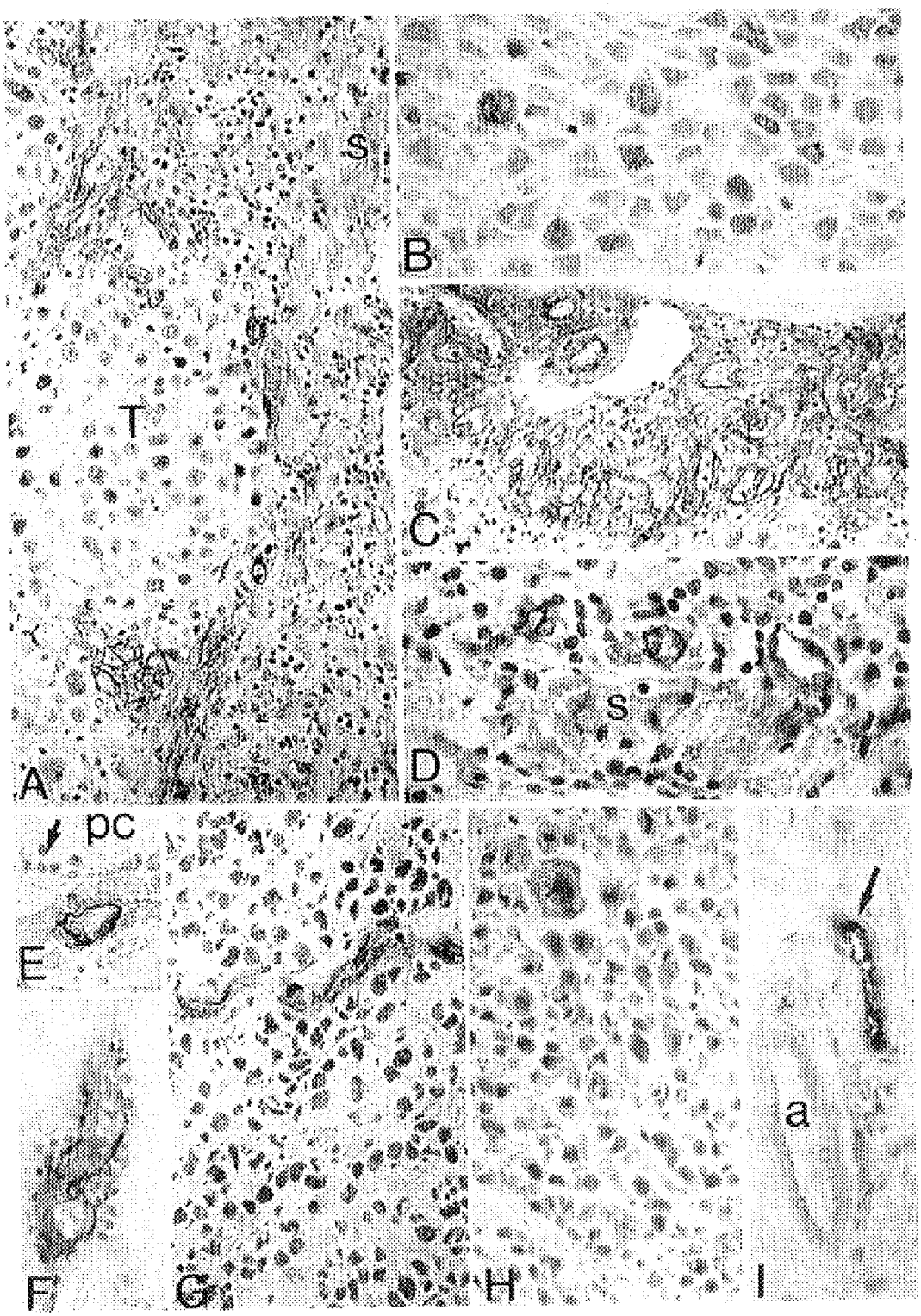
FIGS. 2A–2I are photographs showing the immunohistochemistry of line 10 and line 1 guinea pig bile duct carcinomas and a human large cell lymphoma using antibodies directed against guinea pig or human peptide sequences.

The present invention is an improved immunological preparation comprising not less than two different and distinct types of conjugate molecules in admixture, each type in the admixture being able to bind specifically within a spatially exposed region of VPF which is previously bound in-vivo to the endothelial cells (EC) of a tumor-associated blood vessel. Each conjugate molecule type comprising the immunological admixture is composed of an anti-VPF antibody binding portion which is specific for and will bind selectively to a spatially exposed epitope (or antigenic determinant) existing within a spatially exposed region of the bound in-vivo VPF; and an effector moiety covalently bound to the anti-VPF binding portion, thereby forming a conjugate composition. In this manner, the immunological preparation provides multiple conjugate molecule types in admixture, each of which is able to bind specifically to a different and distinct epitope presented by and existing within at least one topographically available and spatially exposed region of the VPF as bound in-vivo to a tumor-associated blood vessel. The improved immunological preparation thus provides many advantages, benefits, and capabilities not previously known or available. These include the following:

1. The present invention employs anti-VPF antibodies, antibody fragments and specific binding portions of antibodies which are raised against epitopes, or haptens, or antigenic determinants which exist at the peripheral surface and within the spatially exposed regions of VPF bound in-vivo. Only three contiguous regions of in-vivo bound VPF have been identified as being topographically available and spatially exposed. These include particular amino acid residue sequences of VPF existing at specified position numbers for each of the four variant types of the VPF structure. The conjugate molecules of the present immunological admixture thus will bind to the bound VPF under in-vivo conditions because the specificity of the antibody binding portion of the conjugate is selective for only those epitopes which are known to be externally exposed and are spatially available for binding after the VPF has itself become bound to fixed receptors on the surface of the endothelial cell.

2. The present invention envisions and intends that the unique immunological admixture of different conjugate molecule types will be able to bind to different epitopes within a single spatially exposed region or to different epitopes within alternative exposed regions of the VPF structure. Thus, the mixture of conjugate molecules may be specific for a single region or for several different regions of the VPF bound in-vivo—so long as each epitope and each region remains spatially exposed and topographically available after binding in-vivo. The user may then chose which exposed epitopes and which spatially available regions are most suitable and desirable in order to achieve his individual purpose and goal.

3. The present improvement intends that different kinds of effector moieties may be used as a component portion of each conjugate molecule type; and that more than one kind of effector moiety may be attached to the spatially exposed region(s) at different and alternative locations within a single in-vivo bound VPF molecule. Thus a radionuclide may be used as a first effector joined to a first antibody binding portion to form a first type of conjugate; and a heavy metal, or an antimetabolite may be a second effector moiety joined to a second antibody binding portion to form a second type of conjugate. The present immunological admixture of different types of conjugate molecules will thus provide for concurrent specific binding to alternative and different spatially exposed epitopes; and thus multiple types of effectors having different mechanisms of action and providing a range of modulating or disruptive effects can be achieved subsequently when the bound VPF is acted upon or internalized by the endothelial cell in-vivo. In this manner, several different kinds of effector moieties may be concurrently utilized to advantage in order to modify or disrupt the tumor associated blood vasculature.

4. The present improvement intends that a greater concentration of anti-VPF conjugate molecules become bound to the spatially exposed regions of VPF in-vivo than was possible previously. By directing the specificity of each conjugate molecule type to different epitopes and/or different regions concurrently or simultaneously, a far larger number of effector moieties will become fixed to the spatially exposed regions of VPF; and a substantially greater number of effector moieties, both in concentration and variety, will interact with and/or subsequently become internalized within the living endothelial cells of the tumor associated blood vessel. The markedly increased concentration of effectors able to be introduced and to be joined to the VPF in-vivo thus meaningfully enhances the efficacy of the present invention.

5. The present invention may be used for a variety of different purposes and goals. The immunological preparation disclosed herein may be employed solely for human diagnostic purposes if so desired. Alternatively, the admixture of two or more conjugate molecules may be formulated solely for human therapeutic goals. However, via the admixture requirement for the preparation, it is equally intended and envisioned that one type of conjugate molecule be formulated for a first purpose—such as a diagnostic goal, whereas the second conjugate molecule is formulated for a second and different purpose—such as a therapeutic result. In this manner, the present invention may be prepared as a single preparation intended for multiple purposes and achieve several different results concurrently.

6. The present improved immunological preparation may also be usefully employed for a variety of different research purposes—such as determining the relationships between VPF bound in-vivo and the solid tumor matrix internal and microvasculature. The multiple types of conjugate molecules comprising the admixture can and will provide detailed information and knowledge regarding the different functions and actions of specific amino acid residue sequences comprising the dimeric VPF structure; and will also be a guide and tracer by which to follow the VPF molecule after endocytosis and lysis by the endothelial cell in-vivo. The molecular and cellular events caused by internalized VPF may then be recognized and identified using the present invention to advantage.

For ease of comprehension and an appreciation of the unique merits of the present invention, the detailed description of the invention will be disclosed as separate sections presented seriatim as follows: The underlying basis of the invention; a description of the component parts for the conjugate molecule; methods for preparing each type of conjugate molecule; general use parameters and considerations for the invention; and experiments and empirical data evidencing the subject matter as a whole which is the present invention. Each will be described in detail hereinafter.

I. Underlying Basis of the Invention

The reader is presumed to be familiar and well acquainted with the published scientific reports and the patent literature regarding VPF, its functions, its attributes, and its relationship to tumor angiogenesis. However, among this large body of information known and accumulated to date, it is often difficult, if not impossible, to focus upon unusual features and critical observations which lead to unforeseen developments and new innovations within the field. A summary review of the scientific and evidentiary basis for the present invention will therefore provide a factual background for recognizing the unique and unforeseen aspects and improvements provided by the present invention.

A. The VPF Bound In-vivo

First and foremost, the VPF bound in-vivo to the surface receptors of endothelial cells of tumor-associated blood vessels (the initial finding of which is the subject matter of the parent invention and the continuing priority patent applications) is that secreted and mobile VPF which subsequently concentrates and binds selectively to the endothelium and basement membrane of tumor-associated blood vessels in a far greater degree than is found in normal blood vasculature and normal organs and tissues. By definition, "tumor-associated blood vessels" are those blood vessels lying immediately adjacent to and within about 0.5 millimeters from the solid tumor mass and its microvasculature. Tumor-associated blood vessels include both pre-existing and those newly induced by angiogenesis; and provide endothelial cells ("EC") which bear surface receptors (such as flt-1 and kdr) as well as heparin-containing proteoglycans on the cell surface.

It will be recalled that the VPF molecule is not synthesized by the endothelium of a blood vessel. To the contrary, VPF is synthesized, secreted, and released as a mobile entity by the tumor cells forming the tumor mass. VPF is not expressed by either normal or tumor blood vessels; and the VPF bound in-vivo on the endothelium cell surface is solely the result and consequence of previously mobile VPF that had been synthesized and secreted by the nearby tumor cells alone.

The entirety of the VPF which is the objective and the intended target of the present invention, is and must be solely VPF bound in-vivo to the endothelial cells of at least one tumor-associated blood vessel. Should freely circulating VPF be present in any meaningful concentration within the blood of the living subject, such circulating and unbound VPF is uninvolved and is unrelated to the means of action, the utility, and the purposes of the present invention. It is, therefore, an essential requirement of the present invention that the VPF in question be bound in-vivo in each and every instance to the surface of the endothelium in a blood vessel lying immediately adjacent to the solid tumor mass itself.

The priority parent applications (U.S. Ser. No. 779,384 filed Oct. 18, 1991, now abandoned, and U.S. Pat. No. 5,659,013) rely on this fundamental finding and discovery as the basis for the invention described and claimed within those applications. Similarly, the essential information was reported in multiple scientific publications. These include the following: Dvorak et al., *J. Exp. Med.* 174: 1275–1278 (1991); Dvorak et al., *Cancer Cells* 3: 77–85 (1991); Borwn et al., *Cancer Res.* 53: 4727–4735 (1993); Brown et al., *Am. J. Pathol.* 143: 1255–1262 (1993); Nagy et al., *Cancer Res.* 55: 360–368 (1995); Qu-Hong et al., *J. Histochem. Cytochem.* 43: 381–389 (1995)].

B. Composition and Configuration of In-vivo Bound VPF

Endogenous VPF may be produced in at least four variant forms as a result of alternative splicing of the mRNA. The variants include monomer, single strands of VPF (also known as VEGF) which are respectively 121,165,189, and 206 amino acid residues in length. The precise amino acid sequencing in the primary structure for the four molecular species of VPF (VEGF) is shown by FIG. 1 [reproduced from: Ferrara et al., *Endocrine Reviews* 13: 18 (1992)]. Within FIG. 1 [SEQ ID NOS:1–4 respectively], the identity of each individual amino acid residue in sequence is given by the single-letter code system, as conventionally known and employed routinely in this field.

It will be recognized and appreciated from the information of FIG. 1 that the different amino acid segments include omissions in some instances, particularly in the center area of the molecular structure, thereby causing the shorter length strands. In addition, it is noted and recognized that the secreted and released variants of VPF are generally two of the four: the 121 length variant is secreted and soluble; the 165 length variant is soluble and is the prevalent form which is released. The 189 length variant and the 206 length variant are forms also synthesized and secreted by the tumor cell but are mostly retained by the extracellular matrix of the tumor.

It will also be recognized that the native VPF molecule synthesized and secreted in-vivo in four variant formats is a dimer polypeptide structure composed of two monomer peptide chains joined together by disulphide bonds. As such, the native VPF molecule not only has a primary amino acid structure, but also presents a unique secondary and tertiary structural organization in each instance. Thus, each synthesized and secreted VPF molecule presents a distinctive three-dimensional construction, overall configuration, and spatial orientation; and, consequently, only certain zones or regions of the primary structure for the mobile VPF molecule as a whole will appear at the external boundary and peripheral surface of the three-dimensional entity. Accordingly, only some amino acid residue sequences in the primary structure of mobile VPF are topographically present as surface features and remain spatially exposed at the peripheral surface to the ambient vascular environment.

In addition, when the secreted and mobile native VPF molecule then subsequently becomes bound in-vivo to specific receptors on the surface of the endothelium of a tumor-associated blood vessel, one direct consequence of such in-vivo binding is a marked reduction and loss of external surface area and exposed topographical features for the VPF molecule in-situ. Thus, the in-vivo bound VPF molecule presents a diminished amount of peripheral external surface to the ambient environment in comparison to that of its mobile and unbound VPF counterpart; and the in-situ bound VPF molecule has a more limited access to spatially exposed regions and fewer amino acid residues which are topographically available and exposed at the peripheral surface as antigenic determinants in comparison to the mobile and unbound VPF molecule secreted by the tumor cells in-vivo.

The degree of topographical limitations and surface restrictions for in-vivo bound VPF molecules generally are examplifed and illustrated by the antigenic determinants and surface features of one VPF variant, the 189 residue length form, whose primary structure is recited within FIG. 1. The entire amino acid residue sequence of the 189 length monomer chain of VPF can be arbitrarily divided into different regions; and each individual region segment can be identified by the amino acid residues at specific position numbers. In this manner, the 189 residue chain length may be divided into ten (10) individual regional segments as shown by Table 1 below.

TABLE 1

Amino Acid Sequence Of The 189 Length Variant By Region Segment

| | |
|---|---|
| Region 1: | Nos. 1–26 |
| Region 2: | Nos. 27–48 |
| Region 3: | Nos. 49–65 |
| Region 4: | Nos. 66–84 |
| Region 5: | Nos. 85–101 |
| Region 6: | Nos. 102–119 |
| Region 7: | Nos. 120–141 |
| Region 8: | Nos. 142–159 |
| Region 9: | Nos. 160–170 |
| Region 10: | Nos. 171–189 |

Figure 4:
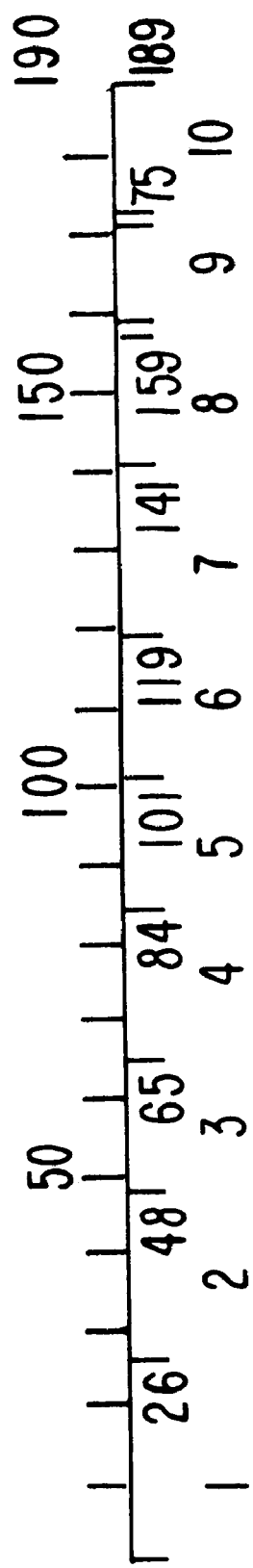
FIG. 4 is an illustration of the 189 amino acid variant of VPF and the peptides forming regions 1–10 respectively.

The regional classification and segmentation of the VPF monomer chain is reproduced graphically in FIG. 4. Moreover, when each individual region of Table 1 is utilized alone for the raising of specific antibodies, two unusual features become recognized: (a) the amino acid sequence of each region individually (1–10 respectively) gave rise to specific antibodies which bound in-vitro to the chosen epitopes; and the antibodies raised against each region (1–10) individually were specific for and bound only to those amino acid sequences selectively. (b) Only three regional antibodies of the ten prepared were able to bind specifically to VPF under in-vivo conditions. This revealed that the other seven regions were either spatially obstructed or topographically internalized within the overall three-dimensional structure and orientation of the native 189 VPF structure; and that only certain regions and a limited number of amino acid residues were available as antigenic determinants in the 189 length VPF molecule after binding in-vivo to the endothelial cells.

The three regions which alone remain spatially exposed to the ambient vascular environment in the native 189 length VPF bound in-vivo are those listed by Table 2 below.

TABLE 2

1st Exposed Region (1):
Amino Acid Sequence Segment, Position Nos. 1–26:
(SEQ ID NO:5)
A P M A E G G G Q N H H E V V K F M D V Y Q R S Y C
(SEQ ID NO:5)
2nd Exposed Region (6):
Amino Acid Sequence Segment, Position Nos. 102–119:
(SEQ ID NO:6)
C E C R P K K D R A R Q E K K S V R 3rd Exposed Region (10):
Amino Acid Sequence Segment, Position Nos. 171–189:
(SEQ ID NO:7)
K A R Q L E L N E R T C R C D K P R R The three externally exposed regions are identified as the amino acid residues of region 1 comprising positions numbers 1–26 respectively; the residues of region 6 comprising position numbers 102–119 respectively; and the segment comprising region 10 offering position numbers 171–189 respectively. The evidence and empirical data supporting this information is provided by Experimental Series II hereinafter and has been previously published in the scientific literature [Sioussat et al., *Arch. Biochem. Biophys.* 301: 15–20 (1993)].

The peripheral surface features and spatially exposed regions described herein for the 189 length are present and are shared by the other variants of VPF as well. The homology of their primary structures is illustrated by FIG. 1; and the well-established properties and functions of native VPF are common to all four variant types. Clearly therefore, the present invention accepts and utilizes the general principle that the topographical and peripheral surface features described above for the 189 length variant are commonly shared among and are present within all four variant forms of the native VPF molecule when bound in-vivo.

Each of the four variant forms of native VPF thus presents three different and distinct, spatially exposed regions of its primary structure to the ambient environment after becoming bound in-vivo to the surface receptors of endothelial cells in a tumor-associated blood vessel. Moreover, each of the three spatially exposed regions found at the periphery surface of the in-situ bound VPF molecule is a particular segment of the VPF primary structure; is of limited length; and is a segment composed of specific amino acid residues in fixed sequences. A listing of the contiguous spatially exposed regions present on the peripheral surface for each variant of VPF bound in-vivo is given by Table 3; and a recitation of the amino acid residue sequence for each spatially exposed region in the 121, 165 and 206 length variant forms of VPF bound in-vivo is given by Table 4.

TABLE 3

Spatially Exposed Regions
Within Variant Forms of VPF Bound In-Vivo

| Spatially Exposed Seguence Segment | VPF Variant Form | Residues at Position |
|---|---|---|
| 1st Region | 121 residue length | Nos. 1–26 |
| 1st Region | 165 residue length | Nos. 1–26 |
| 1st Region | 189 residue length | Nos. 1–26 |
| 1st Region | 206 residue length | Nos. 1–26 |
| 2nd Region | 121 residue length | Nos. 102–115 |
| 2nd Region | 165 residue length | Nos. 102–115 |
| 2nd Region | 189 residue length | Nos. 102–119 |
| 2nd Region | 206 residue length | Nos. 102–119 |
| 3rd Region | 121 residue length | Nos. 116–121 |
| 3rd Region | 165 residue length | Nos. 147–165 |
| 3rd Region | 189 residue length | Nos. 171–189 |
| 3rd Region | 206 residue length | Nos. 188–206 |

TABLE 4

Amino Acid Residue Sequences Of Exposed Regions

VPF 121 Length Variant:
    1st Region Sequence Segment, Position Nos. 1–26:
    A P M A E G G G Q N H H E V V K F M D V Y Q R S Y C  (SEQ ID NO:8)

2nd Region Sequence Segment, Position Nos. 102–115:
    C E C R P K K D R A R Q E K  (SEQ ID NO:9)

3rd Region Sequence Segment, Position Nos. 116–121:
    C D K P R R  (SEQ ID NO:10)

VPF 165 Length Variant:
    1st Region Sequence Segment, Position Nos. 1–26:
    A P M A E G G G Q N H H E V V K F M D V Y Q R S Y C C(SEQ ID NO:11)

2nd Region Sequence Segment, Position Nos. 102–115:
    C E C R P K K D R A R Q E N  (SEQ ID NO:12)

3rd Region Sequence Segment, Position Nos. 147–165:
    K A R Q L E L N E R T C R C D K P R R  (SEQ ID NO:13)

TABLE 4-continued

Amino Acid Residue Sequences Of Exposed Regions

VPF 206 Length Variant:

1st Region Sequence Segment, Position Nos. 1–26:
        A P M A E G G G Q N H H E V V K F M D V Y Q R S Y C   (SEQ ID NO:14)

2nd Region Sequence Segment, Position Nos. 102–119:
        C E C R P K K D R A R Q E K K S V R   (SEQ ID NO:15)

3rd Region Sequence Segment, Position Nos. 188–206:
        K A R Q L E L N E R T C R C D K P R R   (SEQ ID NO:16)

Part of the underlying basis for the present invention therefore is that only three specific regions of a VPF variant bound in-vivo provide spatially exposed antigenic determinants suitable for binding by a specific antibody binding portion of a conjugate molecule. For example, in the 189 length variant, only the amino acid residues in the segments at position numbers 1–26, 102–119, and 171–189 of the in-situ bound VPF molecule remain spatially exposed and topographically available; and any antibody specificity which is directed to another region, amino acid segment portion or antigenic determinant of VPF will fail to be effective and will fail to bind specifically to the VPF molecule bound to the endothelium under in-vivo conditions. As demonstrated and proven by the evidentiary data herein, the use of amino acid residues and polypeptide segments composing the VPF monomer chain which exists outside these three spatially exposed regions will not provide an antibody which is capable or suitable for binding to native VPF disposed on the surface of the endothelial cells of tumor-associated blood vessels.

C. The Unsuitability of the Whole VPF Molecule as an Antigen

The present invention holds and demonstrates that the entire VPF dimer structure and/or monomer chain sequence for any of the four major variant type lengths is undesirable and unsuitable either as an antigen or a haptene for raising specific antibodies and selective antibody fragments which will be able to bind to three-dimensional VPF after it has become bound to endothelial cells in-vivo. The experimental basis and empirical data supporting this conclusion and view is provided by Experimental Series III hereinafter. Accordingly, neither the monomer chain nor the dimer structural form of VPF is preferably employed either as an antigen or haptene because of the three-dimensional configuration and the masking of the VPF molecular surface after binding to its receptor.

Also, it is noted and appreciated that if the entire full amino acid residue length of 121, or 165, or 189, or even 206 residue length is employed, a loss of functional orientation and dimensional form occurs for the whole VPF molecule as the polypeptide lengths are processed and specific antibodies are created in a subject animal. This produces and yields an antibody specificity directed towards those amino acid residue segments which are usually internalized, masked, or spatially obscured after the native VPF molecule becomes bound in-situ to the surface of the endothelial cell in a tumor associated blood vessel. It is, therefore, an explicit requirement, unique feature, and an unforeseen demand of the present invention that the whole monomer polypeptide or dimer sequential residue chains comprising the VPF molecule never be employed as an antigen or haptene for the purpose of raising specific antibodies or antibody derived binding fragments. None of the antibodies raised against the whole VPF molecule are suitable for use with the present invention; and no antibody raised against the whole monomer or dimer VPF molecule is preferably employed in any embodiment of conjugate molecule in this immunological admixture.

II. The Component Parts of Each Type of Conjugate Molecule Comprising the Immunological Admixture The invention is an immunological admixture comprising not less than two types of conjugate molecules, each conjugate type being individually able to bind to an epitope within a spatially exposed region of VPF after it is bound to endothelial cells in-vivo. Each conjugate type is comprised of at least a binding portion of an antibody specific for an epitope found within one of three spatially exposed regions of in-vivo bound VPF—such as are presented by the amino acid residue sequences found at position numbers 1–26, 102–119, and 171–189 in the 189 length variant of VPF. Conversely, this antibody or antibody fragment has no specificity and no capability for binding to any determinant which may exist within the amino acid residue segments typically found outside a spatially exposed region (such as residues at position numbers 27–101 and between numbers 120 and 170 of the 189 length variant). All of these latter segments represent those internalized portions of the VPF molecule which are hidden and spatially obscured within the three-dimensional configuration and orientation presented by the native VPF molecule and after binding to the endothelial cells of tumor-associated blood vessels.

The second component part of each conjugate molecule is the presence of an effector moiety which is covalently bound to the antibody binding portion. By definition, an "effector" is any entity, compound, composition, substance or moiety which causes or generates (directly or indirectly) a physiological or morphological change; and desirably is disruptive, damaging, detrimental, inhibitory, toxic, or suicidal to the endothelium of the tumor-associated blood vessel. It will be recognized and appreciated, therefore, that the end target of the effector moiety is the endothelial cell of the blood vessel lying in close proximity to the tumor solid mass.

The effector moiety thus serves multiple functions and purposes under in-vivo use conditions. Initially, as part of the conjugate molecule adhering to an epitope on the surface of the bound VPF, the effector can act as a surface diagnostic marker and indicator of the native VPF then bound to the surface of the endothelial cell and/or a therapeutic surface agent exerting changes upon the adjacent endothelium. Secondarily, the effector serves as a potential modulator or disrupter of the endothelial cell, whether joined to the surface of the endothelium or when the bound VPF molecule becomes internalized and processed by the organelles of the endothelial cell. Note that the effector moiety concomitantly will become endocytosed as a consequence of the VPF molecule itself being internalized. Another major function and value is the therapeutic result which is obtained when the surface bound VPF is internalized and undergoes internal processing (lysis) by the endothelial cell. The internalized effector moiety will itself become dissociated from the conjugate and activated within the cytoplasm of the endothelial cell by the lytic cell processing system; and the dissociated and/or activated effector will then act to alter, modify, disrupt or otherwise change the normal metabolic, physiological and biochemical processing systems of that endothelium.

In view of the range and diversity of embodiments for each component part of the conjugate molecule, it is desirable to describe each component part in greater detail.

A. The Antibody Binding Portion

The antibody binding portion of each conjugate molecule type must demonstrate the capability of binding specifically to an epitope present within a spatially exposed region of VPF bound in-vivo, such as the antigenic determinants provided by the amino acid residues at position numbers 1–26, 102–119, and 171–189 for the 189 variant of native VPF. However, this binding capability can be demonstrated not only by the whole intact antibody, but also by $F(ab')_2$ fragments, and also by Fab fragments derived from the whole antibody structure. It will be recalled that while the whole antibody is a large bulky protein having two binding sites, the $F(ab')_2$ fragment represents a divalent binding fragment of the whole antibody; while the Fab binding portion is a univalent binding unit having a minimum of antibody structure. In addition, smaller and genetically engineered antibody units having a specific binding capability have also been developed; and these are deemed to be equally suitable for use herein. Methods for preparing, isolating, and purifying each of these different antibody binding segments and units are conventionally known in the scientific literature and have been available for many years as common knowledge in this field. The user may thus chose from among all of these different whole antibodies, antibody subunits and antibody fragments in picking a useful component structure having a specific binding capability for an epitope in one of the spatially exposed regions of the bound VPF molecule.

In addition, the user has the option to chose whether the antibody binding portion is obtained from monoclonal, or polyclonal or broad antisera sources. Equally important, the user will decide whether the source of antibody or antibody fragments should be isolated and purified prior to use in making the conjugate molecule; or whether the antibody containing medium can be employed as a heterogeneous mixture of different entities and varying binding affinities, only some of which will have the requisite affinity and specific binding capability for an exposed epitope on the peripheral surface of the native VPF molecule in-situ. Thus, the degree of homogeneity, of purity, binding and affinity and specificity of antibodies or antibody fragments and genetically engineered subunits for one or more epitopes of bound VPF is left to the discretion and needs of the user.

It will be noted and appreciated also that each of the intended regions for epitope binding within the native VPF molecule provides a large number of potential antigenic determinants within each permissible region spatially available for use. Thus, when choosing an immunogen, it will be recalled that a minimum of 5–7 amino acid residues (in theory) are able to be employed as a hapten in order to raise specific antibodies within a living host animal. However, longer peptide lengths of 10–20 residues are generally preferred. It will be noted also that the three permissible regions in each VPF variant to be used as a source of antigenic determinants each provide far longer amino acid residue segments for this purpose. Thus, for example, in the 189 residue length variant, the first exposed region provides 26 amino acid residues in sequence; the second exposed region provides 19 amino acid residues in sequence; and the third exposed region provides 19 amino acid residues. Thus, even if an extended segment length of 10–20 amino acid residues were purposely employed as the immunogen, a large number of different antigenic determinants becomes available given the range of residue choices even within one permitted region. Accordingly, with the choice of three different and lengthy region segments available to the user, the number of potential epitopes becomes enormous; yet each of these epitopes is a potential specific binding site for the antibody binding portion of the conjugate molecule.

Immunogens

It is intended and envisioned that at least one peptide segment of suitable length (preferably 10–20 residues) be chosen as the immunogen in order to provide the antigenic determinants and the production of specific antibodies using a living host animal. Once the amino acid residue length and composition has been chosen (in conformity with the requirement of being within a spatially exposed region of VPF bound in-vivo), the chosen antigenic or haptene segment must be prepared. Preferably, the desired amino acid segment is synthetically prepared using conventionally known solid phase peptide synthesis methods [such as Merrifield, RB, *J. Am. Chem. Soc.* 85: 2149 (1963)]. Once synthesized, it is most desirable that the chosen segment be purified (such as by gel filtration) and desirably analyzed for content and purity (such as by sequence analysis and/or mass spectroscopy).

After its synthesis, the chosen segment is desirably coupled to a protein carrier to form the immunogen. Conventionally suitable protein carriers available for this purpose are available in great variety from many diverse sources. The only requirements regarding the characteristics and properties of the carrier are: first, that the protein carrier be in fact antigenic alone or in combination with the synthesized chosen amino acid residue sequence; and second, that the carrier protein be able to present the antigenic determinants of the residue sequence such that antibodies specific against the amino acid residues are produced in a living host animal. Clearly, as the experiments described hereinafter, the preferred choice of protein carrier for immunization purposes include keyhold limpet hemocyanin (KLH), coupled by glutaraldehyde (GLDH), sulfo-m-maleimidobenzo (M-hydroxysuccinimide) ester (MBS), or bisdiazobenzidine (BDB). However, any other carrier protein compatible with the host to be immunized is also suitable for use. Example of such other carrier proteins include bovine serum albumin, thyroglobulin, and the like.

Immunization procedure

All immunizations and immunization procedures are performed in the conventionally known manner described in the scientific literature. It is expected that under certain use conditions, adjuvants will be employed in combination with the prepared immunogens. Alternatively, the prepared immunogens may be used alone and be administered to the animal or human host in any manner which will initiate the production of specific antibodies.

In addition, the harvesting of polyclonal antiserum and the isolation of antibody containing sera or antibody producing cells follows the conventionally known techniques and processes for this purpose. Similarly, the preparation of hybridomas follows the best practices developed over recent years for the isolation of monoclonal antibodies [Marshak-Rothstein et al., *J. Immunol.* 122: 2491 (1979)].

Polyclonal and monoclonal antibodies

Once obtained, the polyclonal antisera and/or monoclonal antibodies and/or genetically engineered antibodies should be evaluated and verified for their ability to bind specifically with an epitope existing within a spatially exposed region of native VPF. Also, cleavage with papain will produce two Fab fragments plus the Fc fragment; whereas cleavage of the antibodies with pepsin produces the divalent $F(ab')_2$ fragment and the Fc' fragment—all as conventionally known.

It will be expressly understood, however, that regardless of whether the antibody binding portion represents polyclonal antisera, monoclonal antibodies, the $F(ab')_2$ fragment, Fab fragments, or other antibody subunits—all of these are suitable and intended for use so long as the specific binding capability is demonstrated for at least one epitope within one of the spatially exposed regions of VPF bound in-vivo. It is therefore deemed conventional and expected that a wide variety of different immunoassay systems may be employed to demonstrate the specific binding capability required by the conjugate molecules of the present invention; and that the parameters of concentration, volume, temperature and choice of reagents can be varied extensively at will in the choice of antibodies and/or antibody fragments and subunits employed for this purpose. The present invention therefore presumes and incorporates by reference any conventionally known immunoassay technique, procedure, protocol, or other non-decisive factor or parameter—all of which may be usefully employed for the evaluation and/or preparation of a specific antibody binding portion.

B. The Effector Moiety

The effector portion is a specific entity which is covalently bound to the antibody binding portion to form a conjugate compound. The specific embodiments and choices for the effector moiety will vary and depend upon the intended function and purpose for the effector under the envisioned application or use circumstances. For example, for in-vitro analytical purposes and for in-vivo diagnostic purposes, the effector portion may be an identifying label such as a radioisotope—a radionuclide emitting specific particles or radiations which can be detected by radiography and present an image or localization of the VPF bound in-vivo. A representative but non-exhaustive listing of some analytical and diagnostic radionuclides suitable for use as effector moieties is provided by Table 5 below.

TABLE 5

Analytical and Diagnostic Radionuclides

| Nuclide | Half-life | Decay Mode* |
|---|---|---|
| gallium-67 | 78 hours | E.C. |
| gold–198 | 2.7 days | $\beta^-$ |
| indium-113m | 100 minutes | E.C. |
| iodine-123 | 13.3 hours | E.C. |
| iodine-125 | 60.0 days | E.C. |
| iodine-131 | 8.05 days | $\beta^-$ |
| mercury-197 | 65 hours | E.C. |
| technetium-99m | 6.0 hours | I.T. |
| thallium-201 | 73 hours | E.C. |
| xenon-133 | 5.3 days | $\beta^-$ |

Decay Modes: $\beta^-$ = beta decay; E.C. = electron capture; I.T. = isomeric transition.

In addition, when the conjugate molecule type is to be used therapeutically in-vivo to modulate or injure the endothelium of tumor-associated blood vessels, the effector portion of the conjugate molecule is desirably an active entity which, at the endothelial cell surface or after internalization within the cell, is disruptive and damaging to the metabolic, physiological, or genetic activities ongoing within that endothelial cell. A wide and diverse range of choices therefore exists for therapeutic effector moieties which injure, damage, disrupt or negatively affect the endothelial cell in-vivo. The choices not only include bacterial exotoxins, cytokines, enzymes, active complexes, heavy metals, and specific antimetabolites. Rather, the effector moiety may also take form as a radionuclide having a short half-live duration and acting in any decay mode. For example, alpha particle emitting isotopes may be advantageously used as the effector moiety due to the alpha particle's ability to cause extensive cellular damage within a narrow radius over a very short half-life duration. A representative, but non-exhaustive, listing of therapeutic compounds and compositions suitable for use as effector moieties is given by Table 6; and a representative but non-exhaustive listing of some therapeutic radionuclides suitable for use as therapeutic effector moieties is given by Table 7 below.

TABLE 6

Therapeutic Effector Moieties

A. Bacterial Exotoxins (modified)
- cholera toxin;
- ricin;
- shigella entero toxin
- pertusis toxin;
- tetanus toxin;
- pseudonomos toxin;
- diptheria toxin fragments;
- staphylococcus enterotoxin.

TABLE 6-continued

Therapeutic Effector Moieties

B. Cytokines
    lymphotoxins (LT);
    tumor necrosis factor alpha (TNF-a);
    interleukins (IL-2, 4, 6, 8 or 10);
    interferons (alpha, beta, gamma).

C. Enzymes
    deaminoses; ( cholinesterase
    protease inhibitors ( inhibitors;
    restriction enzymes;
    DNAases;
    RNAases.

D. Active Complexes
    alorin;
    saponins (sapogenin glycosides);
    modeccin;
    gelanin;
    calicheamicin gamma II.

E. Heavy Metals
    zinc;
    copper;
    cadmium;
    mercury;
    lead;
    arsenic.

F. Antimetabolites
    Purine antagonists    (such as 6-mercapato purene, axzthioprine and 6-thioguonine);
    Pyrimide antagonists    (such as 5-fluorouracil, cytosine arabinoside, and bromodeoxy uridine);
    Folic acid antagonists  (such as methotrexate).

TABLE 7

Therapeutic Radionuclides

| Nuclide | Half-Life | Decay Mode* |
|---|---|---|
| chromium-51 | 28.8 days | E.C. |
| cobalt-57 | 270 days | E.C. |
| selenium-75 | 120 days | E.C. |
| phosphorus-32 | 14.3 days | $\beta^-$ |
| ytterbium-169 | 31.8 days | E.C. |
| bismuth-212 | — | A.P.E. |
| astatine-211 | — | A.P.E. |

Decay Mode: E.C = electron capture; $\beta^-$ = beta decay; A.P.E. = alpha particle emitter.

Juncture of the effector moiety

The manner in which the effector moiety is joined to the antibody binding portion will depend on the nature and source of the effector chosen for use in making the conjugate molecule. If the effector moiety is a radionuclide, the radioisotope molecule chosen must be tightly joined to the antibody binding portion either directly or via a bifunctional chelate. The nature of the linkage must be sufficiently strong to endure during the time the conjugate molecule is attached to the bound VPF in-situ on the surface of the endothelial cell; and be sufficiently strong to avoid elution and premature release of the radioactive entity in-vivo. A number of such attachment methods are conventionally known and available in the scientific literature.

Alternatively, if the effector moiety is among those listed by Table 6, or is any other chemically identifiable compound or composition, two general methods of conjugate synthesis are available to the user. The first employs the direct linkage of the effector entity directly or indirectly to the antibody binding portion by covalent chemical reaction. Such reactions may be direct, involve a linker or spacer complex; and/or utilize one or more bifunctional chelating agents as have been described conventionally. Examples of such procedures, techniques, reagents, and protocols are generally described within U.S. Pat. No. 4,867,973—the text of which is expressly incorporated by reference herein. This patent reference as well as the scientific publications cited and specifically identified within this patent document provide a thorough and comprehensive description of all chemical linkage techniques and requirements for forming a conjugate between any chosen effector moiety and the desired antibody specific binding portion described herein.

In the alternative, if the effector moiety is a large polypeptide or a glycopeptide such as a toxin, the fused gene methodology described in detail within U.S. Pat. No. 4,675,382 may also be utilized—the text of this patent also being expressly incorporated by reference herein. The essence of the gene fusion methodology intends that the DNA coding for the antibody specific binding portion and the DNA coding for the effector moiety portion be chemically and physically joined to yield a fused gene; and the expression of the resulting fused gene will yield a conjugate molecule in which a peptide bond serves as the linkage between the antibody specific binding portion and the effector moiety as a whole.

Alternatively again, any other means of covalent linkage effective to join the antibody binding portion and an effector entity together as a conjugate molecule is suitable for use. Such other procedures include derivatizing the specific binding portion with a sulfhydryl reactive group, or a cysteine group, or any other common linking entity which will serve to covalently bind the effector moiety irrevocably. Examples of such procedures are described within U.S. Pat. No. 4,468,382 and the references cited therein, the text of which is expressly incorporated by reference herein.

III. The Conjugate Molecule Types

In general, three broad and different categories of immunological preparations comprising not less than two types of different conjugate molecules can be prepared. For purposes of illustration and ease of comprehension only, each of the three general categories described below will presume the following: (i) That the minimum requirement of two different conjugate molecules in admixture is to be satisfied; (ii) that only two kinds of binding specific antibody fragments are available; and (iii) that only two different effector moieties are suitable for the intended application.

Category 1: This general category will utilize two different types of binding specific antibody portions or fragments and a single type of effector moiety. Each of the antibody binding portions is targeted to and will bind selectively with only one epitope within a spatially exposed region of VPF bound in-vivo; and each epitope is unique for that individual antibody binding portion. There is no requirement, however, that each of the two individual epitopes exist in different regions of the VPF; nor that the epitopes individually be based on or arises from different chemical entities or amino acid residues. All that is required is that two individual and different, spatially available epitopes exist; and that two different and distinct antibody binding portions exist, each of which is able to join with one epitope individually.

In this category instance, a single embodiment of effector moiety may therefore be employed to yield two different types of conjugate molecules. The covalent linkage of the single effector moiety to the first antibody binding portion (specific for the first epitope) will yield a first type of conjugate molecule. In addition, the covalent juncture of the same effector moiety to the second antibody binding portion (specific for the second epitope) will consequentially yield a second type of conjugate molecule. Each of the two different and distinct conjugate types have different and alternative specific binding portions but share in common the same effector moiety within their individual overall composition and structure.

Category 2: The second general category employs two different embodiments of effectors and a single antibody binding portion (specific for a single epitope site alone). For example, the first effector moiety is a radioisotope while the second effector entity is a heavy metal. When these two effector moieties are separately and individually joined to a single embodiment of antibody binding portion, two different and distinct conjugate molecules will result. Each type of conjugate molecule will have a unique and singular effector moiety as part of its overall composition and structure; nevertheless each of the two different conjugate molecules will compete against the other for effective binding and juncture to the same epitope on the spatially exposed region of VPF bound in-vivo. This is a less desirable category in that a competition is created in-vivo between each of the two different conjugate molecule types for the same epitope concurrently.

Category 3: This general category utilizes two different antibody binding portions, each of which is targeted to and will bind specifically with a single epitope on the spatially exposed surface of VPF bound in-vivo. This category also utilizes two different embodiments of effectors in order to make the multiple conjugate molecule types. Thus, the first antibody specific binding portion (targeted to a first epitope) is combined with a first effector moiety. In addition, the second antibody binding portion (specific for a second epitope unrelated to the first epitope) is covalently linked to a second effector moiety. In this manner, two different types of conjugate molecules are produced: each targeted to a different epitope on the spatially exposed surface of bound VPF; and each of the differently targeted conjugate molecule types will bear a different and individual effector moiety as part of its overall composition and structure. This category model of immunological preparation is most desirable because it not only targets multiple epitopes at different locations but also directs different effectors concurrently to the exposed surface of the VPF molecule bound in-situ.

It will be recognized and appreciated that the three categorical models presented herein are merely illustrations examplifying the most basic and fundamental mixtures which utilize a minimum number of specific antibody binding portions and effector moieties. Nevertheless, each general category represents a different manner of immunological preparation and provides not less than two types of conjugate molecules in admixture which are distinctly different from each other. Clearly, the number of conjugate type variations may be increased geometrically; and each of these model categories can be expanded and diversified at will in order to create many more combinations of antibody binding portions and effector moieties—each of which will meet and satisfy the minimal requirements of the present invention.

IV. Use Parameters and Other Considerations

Although the immunological preparation comprising the present invention may be broadly prepared in a variety of vastly different and highly divergent embodiments utilizing many different types of conjugate molecules in admixture conforming to the requirements described herein, several useful operational parameters and general considerations may be taken into account in order to maximize its value and utility in the intended application. The listing provided below represents suggestions, options, and recommendations for the intended user. These considerations are not, in any sense, to be viewed or deemed as restrictions, requirements, or limiting factors to any desired use or envisioned application of the present invention.

1. It is generally desirable and preferable that more than one epitope be employed as the target on the spatially exposed surface of the VPF molecule bound in-vivo; and it is most desirable that the multiple epitopes be located in different spatially exposed regions rather than lie within a single spatially exposed region of the VPF molecule in-situ. The underlying consideration for this preferred use parameter is that the prepared conjugate types in admixture will each present an antibody specific binding portion, subunit, or fragment as the means for targeting each individual epitope; and even if one of the smallest of these, the Fab univalent fragment is employed, the typical Fab fragment (having a specific binding capacity) nevertheless will present a substantial size, three-dimensional configuration, and volume. It is therefore desirable that as much distance and topographical space as possible exist between the chosen individual epitopes on the spatially exposed surface of the VPF molecule in-situ to accommodate the size and bulk of each specific antibody or binding fragment comprising each type of conjugate molecule. Note that the present invention intends and permits the use of multiple epitopes within a single exposed region—that is, many different epitopes will co-exist and be located within a single spatially exposed region—such as, for example, within positional numbers 1–26, or 102–119, or 171–189 respectively of the 189 length variant; and sufficient distance between multiple epitopes within a single one of these exposed regions is both envisioned and desirable such that two or more conjugate molecule types can spatially fit and bind within a single region of the VPF molecule in-situ. Nevertheless, in order to provide for a more diverse sizing and more heterogeneous mixture of conjugate types, it is most desirable to target epitopes lying in different regions concurrently; and therefore allow a broad, size accommodating collective of epitope binding sites which are spread over the entire spatially exposed peripheral surface of the bound VPF.

2. It is generally desirable that as large a variety of antibody binding portions as possible be utilized; and that the specific antibodies or antibody fragments bind to different epitopes—each epitope being spatially exposed on the surface of the VPF molecule after being bound in-vivo. For this purpose, polyclonal antisera offer an advantage over single monoclonal antibodies; but purposefully prepared mixtures of different monoclonal antibodies are deemed to be most desirable for use. Similarly, for size and bulk considerations, it is most desirable that the polyclonal antisera or monoclonal antibodies be cleaved to antibody fragments; and most desirably be digested into the univalent Fab fragment or a smaller antibody subunit which will bind selectively to a single epitope. In this manner, not only will a diverse range of specific binding conjugate molecules be prepared, but also this immunological admixture can be targeted towards multiple epitopes lying in different spatially exposed regions of the VPF molecule in-situ. In this manner, a greater density of conjugate molecule juncture and attachment to the VPF bound in-vivo can be achieved; and a far greater portion of the topographically available, spatially exposed surface of the VPF molecule after binding can be utilized for the targeting of many different types of conjugate molecules concurrently and simultaneously.

3. It is believed that a variety of different effector moieties should be used concurrently in order to make as diverse a mixture as possible of differing conjugate molecule types. In addition, it is also expected that each of the chosen effector moieties (regardless of the range of diversity) should be as small as possible in physical size and bulk as can be managed under the intended use circumstances. For this reason, the kind of effector moiety envisioned to be most effective are the radioisotopes having differing modes of decay and individual half-live durations. Another very useful kind of effector is examplified by the available antimetabolites of Table 6—these also being of more limited size and three-dimensional configuration. All of these preferred effector moiety embodiments present a minimal size, volume, and the least bulk possible for the resulting conjugate molecules employed in admixture.

4. It is also envisioned and intended that in-vivo applications using the present immunological preparation will be directed to different functions concurrently and serve different purposes over time. For example, with a particular human patient, it is often desirable to monitor the delivery of a therapeutic molecule. For this purpose, it is desirable to include in the same treatment particular molecules that (a) permit visualization, and (b) are cytotoxic. By carefully choosing and preparing two or more conjugate molecules., each of which comprises a different kind of radioisotope, both a diagnostic conjugate molecule and at least one therapeutic conjugate molecule can be prepared and combined in admixture as a single preparation. This admixture of different conjugate molecule types will be administered to the patient as a single immunulogical preparation; but will provide multiple purposes and results over time for that subject. For example, the different conjugate molecules may utilize a first conjugate employing the gold-198 with its antibody binding portion; while a second conjugate molecule type might use technetium-99m with a second antibody binding fragment; and even a third type of conjugate molecule may be utilized having astatine-211 as its effector moiety. Each of the three conjugate molecule types utilizes a different radioisotope having an individual mode of decay and having a markedly different half-life span. The user of this immunological preparation may then follow the progression of effects in -vivo not only as a function of time; but also by the diagnostic visualization and therapeutic effects provided by each of the different radioisotopes within each conjugate molecule type.

V. Experimental and Empirical Data

To demonstrate the merits and value of the present invention, a series of planned experiments and empirical data are presented below. It will be expressly understood, however, that the experiments described and the results provided are merely the best evidence of the subject matter as a whole which is the invention; and that the empirical data, while limited in content, is only illustrative of the scope of the invention envisioned and claimed.

Experiment Series A*

* Reproduced from: Dvorak et al., *J. Exp. Med.* 174: 1275–1289 (1991).

Materials and Methods

Animals, Tumors and Antipeptide Antibodies

Ascites variants of chemically induced guinea pig line 1 and in line 10 bile duct carcinomas were passaged in the peritoneal cavities of inbred strain 2 guinea pigs. To form solid tumors, $3\times10^6$ washed ascites tumor cells were injected subcutaneously into 400 g strain 2 guinea pigs. To identify leaky blood vessels, colloidal carbon was injected intravenously 30 min before tumor harvest using the procedure of Dvorak et al. [*Am. J. Pathol.* 133: 95 (1988)]. Autochthonous human tumors were obtained after surgery.

The $NH_2$-terminal 25-amino acid sequence of guinea pig VPF, here designated peptide 1A and expressed in single letter code, is APMAEGEQKPREVVKFMDVYKRSYC [SEQ ID NO:17]. The 26-amino acid $NH_2$ terminus of human VPF (peptide 1B) differs from that of guinea pig VPF by the six underlined amino acids: AP-MAEG<u>GG</u>Q <u>NHH</u>EVVKFMDVY<u>Q</u>RSYC [SEQ ID NO:18]. These and an internal peptide (CECRPKKDRARQEKKSVT [SEQ ID NO:19], peptide 6) corresponding to amino acids 102–119 of the 189-amino acid form of human VPF were synthesized, coupled to a protein carrier, and used to immunize rabbits.

Immunohistochemistry and In Situ Hybridization

Guinea pig tissues were fixed in formalin or cardodiimide and embedded in paraffin. Fresh frozen sections of human tumors were fixed in acetone. Immunohistochemistry was performed on 5–7 $\mu$m paraffin or frozen sections, using affinity-purified first antibodies to guinea pig or human VPF peptides and an avidin-biotin peroxidase procedure. Controls included substitution of the first antibody with an unrelated rabbit antipeptide antibody, preabsorption of first antibody with specific peptide, and on-the-slide competition for first antibody with specific peptide.

In situ hybridization was performed using $^{35}$S-labeled single-stranded RNA probes prepared by in vitro transcription of a 204-bp guinea pig VPF cDNA fragment cloned in PGem3Zf(+) [ffrench-Constant et al., *J. Cell Biol.* 190: 903 (1989)].

Experiment 1

Localization of VPF in tumors by immunohistochemistry was performed on growing, 5–8 day solid tumors. The most striking finding was that the new blood vessels induced by both line 1 and line 10 tumors stained consistently and intensely with antibodies to VPF peptides A1 and 6 respectively. The results are shown by FIGS. 2A–2I.

FIG. 2 as a whole reveals the immunohistochemistry of line 10 (A–C, E, F, H and I) and line 1 (D) guinea pig bile duct carcinomas and a human large cell lymphoma (G) with antibodies directed against guinea pig or human VPF peptides: (A–F) peptide 1A; (G) peptide 1B; (H and I) peptide 6. Immunohistochemical reaction product appears yellow-brown. FIG. 2A shows an overview showing minimal staining of line 10 tumor cells (T) with antibody to peptide 1A but intense staining of tumor-associated blood vessels 8 d after transplant. Focally, adjacent stroma (s) is also stained as demonstrated by FIGS. 2B–2D. Higher magnification photographs illustrating variable line 10 tumor cell staining (B) and intense staining of line 10 (C) and line 1 (D) tumor vessels; (s) staining of adjacent stroma. FIG. 2E shows that new, ascites tumor-induced blood vessel of the peritoneal wall stains intensely; attached tumor cells (arrow) are unstained; (pc) peritoneal cavity. FIG. 2F shows that the pre-existing venules of normal skeletal muscle adjacent to a line 10 tumor are strongly stained with antibody to peptide 1A.

FIG. 2G reveals that vessels in a human B cell lymphoma react strongly with antibody to peptide 1B. FIGS. 2H and 2I show the staining of nearly all line 10 tumor cells (H) and a nearby venule (arrow in I) with antibodies to peptide 6. As with antibodies to the VPF $NH_2$ terminus, adjacent venules and small veins (arrow in I) stain intensely, but arteries (a in I) stain faintly or not at all. Magnifications: (A) ×245; (B and D) ×405; (C) ×313; (E, F, and H) ×260; (G) ×320; (I) ×410.

FIG. 2 also reveals several major points: Vessel staining was circumferential and involved EC and vascular basement membranes; sometimes, adjacent extracellular matrix also stained weakly. This is shown by FIG. 2A and 2D. Line 1 tumors underwent cell-mediated immune rejection which was accomplished by a striking and rapid (within 24–48 h) loss of vessel staining (not shown). The rapid depletion of VPF that accompanied tumor destruction suggests rapid turnover of blood vessel-associated VPF. Preliminary studies with antibodies to VPF peptide 1B indicates that human tumors also exhibit VPF staining and in a pattern similar to that of guinea pig tumors (FIG. 2G).

In addition to the tumor microvasculature, vessels coursing through immediately adjacent normal tissues also exhibited specific antibody staining (FIG. 2F). Immunoreactive vessels were venules and small veins within ~0.5 mm of tumors; arterioles, capillaries, and vessels of any type at greater distances from tumor or in other tissues and organs exhibited no staining. Consistent with these findings, antibodies to VPF peptide 1A also stained immediately adjacent, preexisting host venules and small veins as early as 5 h after tumor cell transplant. These preexisting blood vessels, as well as induced tumor vessels, were hyperpermeable as judged by their concentration of circulating colloidal carbon.

Experiment 2

The tumor cells were then evaluated for the ability to synthesize VPF. It was noted that a minority of tumor cells stained with antibody to VPF peptide 1A, but nearly all tumor cells stained with antibody to peptide 6. The tumors were therefore subjected to in-situ hybridization with $^{35}$S-labeled single stranded RNA probes. The results are provided by FIGS. 3A–3C respectively.

Figure 3:
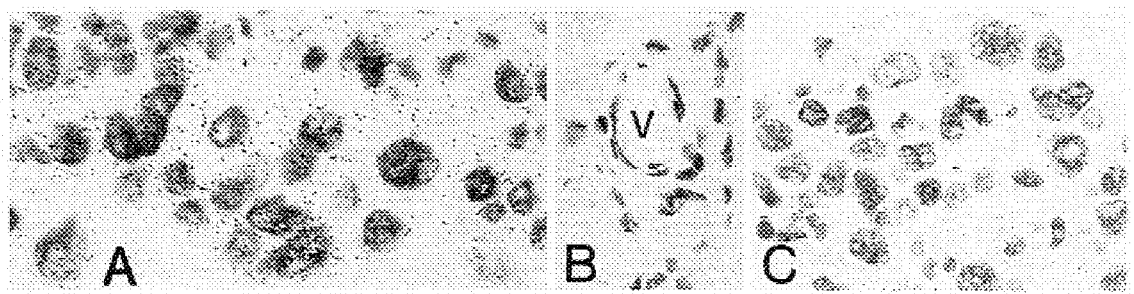
FIGS. 3A–3C are photographs illustrating autoradiographs of in-situ hybridization of solid line 10 tumors with $^{35}$S-labeled antisense and sense probes to guinea pig mRNA for expression of VPF.

FIG. 3 provides autoradiographs representing in situ hybridization performed on sections of solid line 10 tumors with $^{35}$S-labeled antisense (FIGS. 3A and 3B) and sense (FIG. 3C) RNA probes to guinea pig VPF mRNA. With antisense probes, labeling is observed over nearly all tumor cells (A) but not over adjacent microvessels (v in B). Autoradiograph exposure times were selected to permit clear visualization of cells I underlying grains. With the corresponding sense probe (C), tumor cells are not labeled, even after lengthy exposures. Magnifications: (A) ×500; (B and C) ×385. Thus, using in situ hybridization nearly all line 10 solid or ascites tumor cells reacted with the antisense RNA probe for guinea pig VPF mRNA; however, tumor blood vessels were negative for VPF transcript.

Conclusions

1. The data clearly indicates that VPF is abundantly synthesized by tumor cells but not detectably by EC; therefore, the VPF identified in tumor-associated vessels reflects selective binding of tumor cell-secreted VPF. Also, with regard to the precise vascular structures to which tumor cell-secreted VPF bound, EC have receptors for VPF and it is believed that the staining represents VPF that has bound to the EC surface or that has been subsequently internalized.

2. The intense tumor-associated vessel labeling observed with anti-VPF peptide antibodies was unexpected. VPF exerts its effects on vascular endothelium at low nM to sub-pM concentrations, well below those detectable by immunohistochemistry; e.g., staining could not be demonstrated when VPF was injected into normal guinea pig skin in amounts sufficient to increase local vascular hyperpermeability. Therefore, VPF accumulates in tumor-associated blood vessels in amounts much greater than those necessary to trigger vascular responses. Tumor-associated vessel binding provides a mechanism for retaining and concentrating VPF, thereby maximizing its activity locally while preventing its spread to more distal sites.

3. Finally, it should be noted that VPF immunostaining distinguishes tumor-associated blood vessels from those found elsewhere in tumor-bearing or control animals. This finding stands in contrast to the widespread distribution of other factors such as bFGF in vascular basement membranes of normal tissues. Bound VPF provides a new marker for tumor blood vessels and may offer a useful target for imaging and therapy.

Experimental Series B[f]

[f] Reproduced from: Sioussat et al., *Arch. Biochem. Biophys.* 301: 15–20 (1993).

Methods and Materials

Materials:

All materials were from Sigma Chemical Co. (St. Louis, Mo.) except as otherwise noted. The guinea pig VPF used in this study was obtained from the conditioned media of cultured guinea pig line 10 carcinoma cells after either one (heparin-Sepharose, Pharmacia, Piscataway, N.J.) or two (heparin-Sepharose and hydroxylapatite chromatography) purification steps. The human VPF used in this study was partially purified from conditioned media of methyl-N-nitrosoguanidine-treated human osteosarcoma cells by heparin-Sepharose chromatography and then concentrated by vacuum dialysis (Schleicher & Schuell, Keene, N.H.).

Peptides:

A diagram of the peptides to which antibodies were generated is shown in FIG. 4. Immunizing peptides were constructed as shown in Table E1. These corresponded to both the N- and C-termini and to a series of internal sequences each designed according to criteria which included the locations of VPF splice sites, an optimum peptide length for antigenicity, hydrophilicity, and mode of conjugation for immunization. The first 26 amino acids of the N-termini of guinea pig and human VPF differ by 6 amino acids. Therefore, in addition to the peptide previously constructed to simulate the guinea pig N-termini (peptide 1a), a peptide also was made corresponding to the human VPF N-termini (peptide 1b).

The immunizing peptides are desirably at least 10 amino acids long to insure an efficient immune response; and optimally are 12 amino acids in length. Beyond this number, immunogen reactivity is variable, but becomes independent of peptide length. Each peptide in this study was thus purposely chosen to be at least 17 amino acids long, and units of secondary structure will be therefore retained and present within most of the immunizing peptides. Peptide secondary structure is useful for an immunogen because antibodies to proteins are often raised against three-dimensional topographies rather than against linear amino acid sequences. The peptides employed herein were synthesized by Multiple Peptide Systems (San Diego, Calif.); the C-termini of all but the C-terminal peptide was amidated.

Internal peptides had their C-termini blocked with amides. Coupling to KLH was achieved through: MBS, crosslinks cysteine to KLH; GLDH, crosslinks primary amino groups to KLH; BDB, crosslinks tyrosine to KLH (tyrosine added to N-terminus of peptides 9 and 10 for this purpose). Peptide 1a represents the N-terminal sequence of guinea pig VPF; 1b represents the N-terminal sequence of human VPF and 2–10 constitutes the remainder of the human VPF sequence.

adjuvant 1 month later (5). Peptides were coupled to cyanogen bromide-activated Sepharose or thiopropyl Sepharose columns (Pharmacia) for affinity purification of antibodies. The protein concentration of the affinity-purified antibodies was determined by the absorbance at 280 nm, using an extinction coefficient of 1.5 ml/mg cm. All affinity-purified antibodies had a concentration of between 0.1 and 1.1 mg/ml, typically ~0.5 mg/ml, depending on the mode of peptide coupling to the support for purification. Antisera and affinity-purified antibodies were tested for activity against their respective peptides by ELISA with 10% normal human serum as a blocking agent. ABT (2,2'-azino-di-[3-ethylbenzothiazoline sulfonate], Kirkegaard & Perry Laboratories, Inc., Gaithersburg, Md.) was the enzyme substrate and color development was determined on a Molecular Devices THERMOmax microplate reader at 405 nm.

Antibody absorption of VPF and Miles vessel permeability assay.

Solid-phase immunoadsorption of guinea pig and human VPFs was performed with antisera and affinity-purified antibodies attached to protein A-Sepharose as previously described [Senger et al., *Cancer Res.* 50: 1774–1778 (1990)]. Adsorbed supernatants and other samples were

TABLE E1

| VPF Region | Peptide Immunogen No. | Composition of Immunogen |
|---|---|---|
| 1 | 1a | APMAEGEQKPREVVKFMDVYKRSYC(-MBS-KLH)(SEQ ID NO:20) |
| 1 | 1b | APMAEGGGQNHHEVVKFMDVYQRSYC(-MBS-KLH)(SEQ ID NO:21) |
| 2 | 2 | HPIETLVDIFQEYPDEIEYLFK(-GLDH-KLH)(SEQ ID NO:22) |
| 3 | 3 | (KLH-GLDH-)PSCVPLMRCGGCCNDEG(SEQ. ID. NO:23) |
| 4 | 4 | (KLH-GLDH-)LECVPTEESNITMQIMRIK(SEQ. ID NO:24) |
| 5 | 5 | (KLH-GLDH-)PHQGQHIGEMSFLQHNK(SEQ ID NO:25) |
| 6 | 6 | (KLH-MBS-)CECRPKKDRARQEKKSVR(SEQ ID NO:26) |
| 7 | 7 | GKGKGQKRKRKKSRYKSWSVPC(-MBS-KLH)(SEQ ID NO:27) |
| 8 | 8 | GPCSERRKHLFVQDPQTC(-MBS-KLH)(SEQ ID NO:28) |
| 9 | 9 | (KLH-BDB-)(Y)QTCKCSCKNTDSRCKAR(SEQ ID NO:29) |
| 10 | 10 | (KLH-BDB-)(Y)KARQLELNERTCRCDKPRR(SEQ ID NO:30) |

Preparation of antibodies and ELISA

Peptides were coupled to key-hole limpet hemocyanin (KLH, Calbiochem, San Diego, Calif.) via glutaraldehyde (GLDH, Electron Microscopy Sciences, Fort Washington, Pa.), sulfo-m-maleimidobenzo (N-hydroxysuccinimide) ester (MBS, Pierce Chemical Co., Rockford, Ill.) or bisdiazobenzidine (BDB), depending on peptide composition and terminal amino acids, to ensure maximum exposure of the peptide epitopes. GLDH, which crosslinks primary amines, may destroy epitopes on peptides having internal lysines; therefore only peptides 2, 3, 4, and 5, which lack lysines, were conjugated with GLDH. MBS was used to link terminal or near-terminal cysteines with KLH. Peptides 9 and 10 have internal cysteines and lysines so an $NH_2$-terminal tyrosine was added during peptide synthesis so these peptides could be conjugated to KLH with BDB. No special effort was made to maintain cysteine-containing peptides in the reduced form.

As shown by the peptide designation and regional divisions of FIG. 4, immunogenic peptide 9 overlaps with 8 and 10. The shortest hash marks delineate 9; 16 longest, 10; midsize, 8 and other peptides. The number in the protein sequence of the C-terminal residue of each peptide is indicated by the hash marks.

Immunization Procedure

Rabbits were immunized with peptide-KLH conjugates plus free peptide (1 mg) in complete Freund's adjuvant and boosted with the same immunogen in incomplete Freund's tested for VPF activity in the Miles vessel permeability assay on depilated, adult Hartley guinea pigs following i.v. injection of Evans blue dye [Senger et al., *Science* 219: 983–985 (1983); Miles, M and E. M. Miles, *J. Physiol.* (London) 118: 228–257 (1952)]. Solutions containing >0.1 nM VPF gave unequivocal positive reactions within 5 min. Affinity-purified antibodies were tested for their capacity to block human VPF singly or in pairs by incubating VPF with different concentrations of antibodies at room temperature for 30 min prior to testing in the Miles assay. VPF adsorption and initial assessments of VPF permeability blocking activity by antibodies were graded by estimating the intensity of the blue skin test site on a scale of 0 to +4. In some cases, permeability activity was quantiated by extracting the dye from individual skin test sites with formamide (Fisher Chemical, Fair Lawn, N.J.) at 45° C. for at least 7 days and measuring the absorbance of the filtered extract at 620 nm [Udaka et al., *Proc. Soc. Exp. Biol. Med.* 133: 1384–1387 (1978)]. Phosphate-buffered saline (PBS), the diluent for all skin test samples, was injected into control sites and served as a background control, which was subtracted from the absorbance of all extracts derived from the same guinea pig. An antipeptide antibody raised to 20 amino acid peptide which bore no relation to any of the VPF peptides served as a negative control.

Electrophoresis and immunoblots

Human or guinea pig VPF was subjected to SDS-polyacrylamide gel electrophoresis in 12% gels under reducing conditions. Gels were transferred to immobilon (Millipore, Bedford, Mass.) and stained with antisera or affinity-purified antibodies, with 3% hemoglobin and 0.05% Tween 20 as blocking agents, with the ABC method (Vector Laboratories, Burlingame, Calif.) and with 3,3'-diaminobenzidine-HCl as the enzyme substrate. To determine the specificity of antibody binding, in some experiments, peptides were included to block antibody binding to VPF; peptides were mixed with the undiluted antibody for 15 min at room temperature prior to dilution and incubation with the blot.

Experiment 3

Initially, the binding specificity of the antisera was evaluated. ELISA demonstrated that each of the 11 peptide-KLH conjugates elicited antisera which, when diluted >10,000-fold, reacted against the respective immunizing peptides. Antisera also were tested for reactivity with VPF on immunoblots and in an immunoadsorption assay. Immunoblots were performed on reduced human or guinea pig VPF and similar results were obtained with both, although a relatively low concentration of human VPF in the immunoblotted samples gave rise to weaker staining compared with immunoblots of guinea pig VPF. The results are shown by FIGS. 5A and 5B.

Figures 5A, 5B:
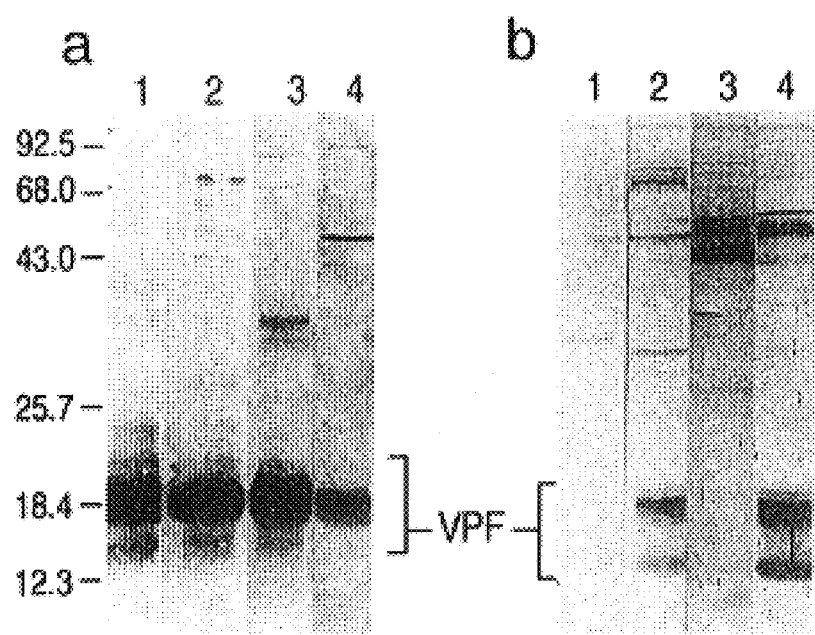
FIGS. 5A and 5B are photographs showing immunoblots of VPF stained with antipeptide antera.

As seen in FIG. 5, partially purified reduced VPF was electrophoresed on a 12% SDS gel and transferred to immobilon. The immunoblots were stained with antipeptide antisera. Preimmune sera and antisera preincubated with the corresponding peptides served as controls. FIGS. 5A and 5B show guinea pig VPF stained with: lane 1, antiserum to peptide 1a; lane 2, antiserum to peptide 2; lane 3, antiserum to peptide 5; lane 4, antiserum to peptide 10. (Peptide and preimmune sera controls, not shown.) Some of the high molecular weight bands stained here were also stained by preimmune serum or were not stained consistently and when different blocking agents were used. The major high molecular weight band stained in lane 4 may represent cross-reactivity of another protein in this crude VPF preparation with this antibody.

In comparison, FIG. 5B shows human VPF stained with: lane 1, preimmune serum of rabbit immunized with peptide 1b; lane 2, antiserum to peptide 1b; lane 3, preimmune serum of rabbit immunized with peptide 2; lane 4, antiserum to peptide 2. The overall staining of human VPF with antibodies is weaker due to the relatively low amount of human VPF on the blots.

Conclusions:

The antisera to peptides 1a, 1b, 2, and 5 reacted strongly with both guinea pig and human VPF and the antiserum to peptide 10 reacted strongly with guinea pig VPF. The antisera to peptides 6, 7, 8, and 9 reacted weakly with guinea pig VPF, but not detectably with human VPF. Peptides 7, 8, and 9 correspond to regions encoded only in a subset of VPF mRNA splicing variants which might be expressed variably by different species and cells and may be present only at low levels in the VPF preparations we studied. The antisera against peptides 3 and 4 reacted with neither human nor guinea pig VPF on immunoblots. Similar results were obtained for immunoblots with affinity-purified antibodies (not shown).

Experiment 4

Antibodies to each peptide were affinity-purified and tested for their ability to bind native VPF. Each antibody was bound to protein A-Sepharose and used to adsorb native VPF from solution. The unbound VPF was detected with the Miles vessel permeability assay.

IgG of each affinity-purified antibody was adsorbed onto protein A-Sepharose and was incubated with VPF at dilutions suitable for testing in the Miles permeability assay. Supernatants remaining after removal of the VPF-antibody-bound beads by centrifugation were tested for residual VPF activity and scored against VPF which had been incubated with Sepharose beads adsorbed with affinity-purified antibodies to an unrelated peptide. The amount of activity was scored on a scale of 0 (no activity) to 4 (maximal activity). The results are given by Table E2 below.

TABLE E2

Remaining VPF Permeability Activity After Adsorption to Immobilized Affinity-Purified Antipeptide Antibodies

| Antibody to peptide number | VPF activity remaining raw score, scale 0 to 4 | |
|---|---|---|
| | Guinea pig | Human |
| 1a | 0 | 0 |
| 1b | 0 | 0 |
| 2 | 3 | 3 |
| 3 | 4 | 4 |
| 4 | 4 | 4 |
| 5 | 4 | 4 |
| 6 | 2 | 2 |
| 7 | 4 | 4 |
| 8 | 2 | 4 |
| 9 | 2 | 4 |
| 10 | 1 | 0 |
| Control | 4 | 4 |

Conclusions:

Five of the 11 antisera (to peptides 1a, 1b, 2, 6, and 10) adsorbed some or all activity of both human and guinea pig VPF. The antibodies to peptides 2 and 5 adsorbed native VPF less well than might have been predicted by their strong staining of denatured and reduced VPF on immunoblots, suggesting that these amino acid sequences are poorly exposed in the native molecule or, alternatively, that they exist in complex higher order structure. Antisera to peptides 8 and 9, sequences present only in the 165 and 189 amino acid polypeptides encoded by alternatively spliced mRNAs, adsorbed guinea pig, but not human VPF, suggesting that the human VPF employed in this study contained predominantly the shortest (121 amino acid) variant, while the guinea pig VPF contained a longer variant(s).

Experiment 5

Antibodies to peptides represented in all three of the major alternatively spliced variants of VPF then were tested for their ability to diminish VPF activity when coinjected with VPF in the Miles permeability assay. Because guinea pigs may express hypersensitivity to whole rabbit sera, antibodies were affinity-purified before testing.

Figure 6:
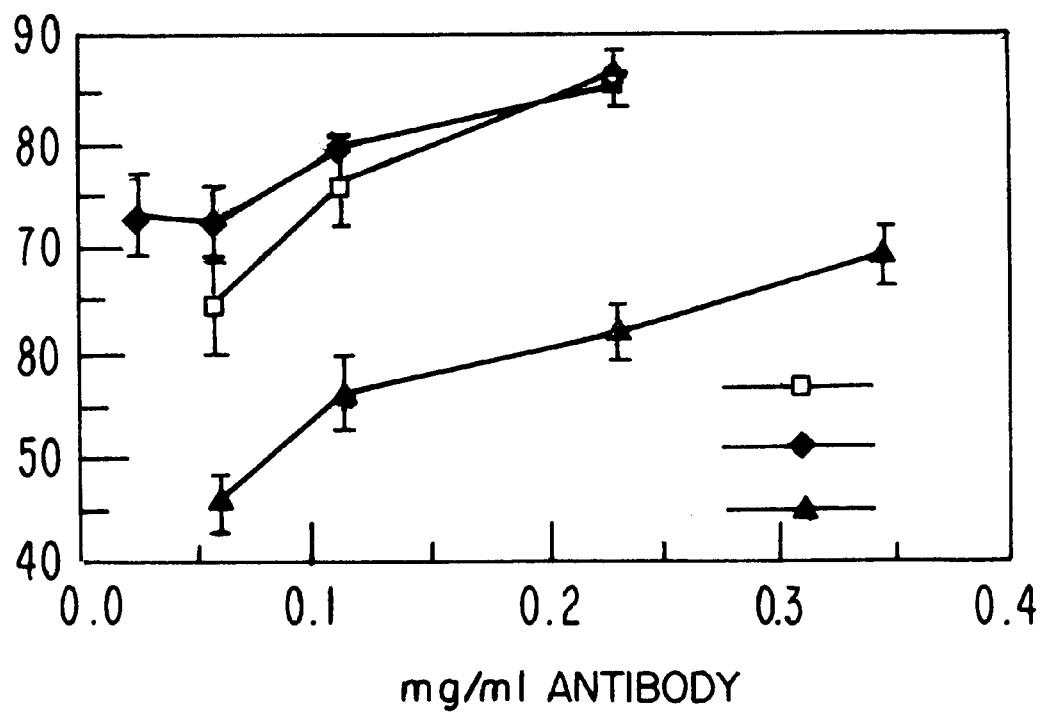
FIG. 6 is a graph showing the blocking of VPF permeability activity by varied concentrations of antibodies raised against regional peptides.

FIG. 6 shows the blocking of VPF permeability activity by varied concentrations of antibodies to peptides. Quantitation of the extent of reduction of permeability induced at Miles test sites, using human VPF and varied amounts of affinity-purified antibodies to peptides 1a, 1b, and 10. Absorbance of extracted dye (see Materials and Methods) was corrected with that from sites injected with PBS and compared with that from sites injected with VPF alone. % block of permeability is expressed as mean ±SE for each amount of antibody per injection.

Results:

Only antibodies to peptides representing N- and C-termini showed substantial blocking activity. Specifically, antibodies to peptides 1a and 1b, and to a lesser extent 10, efficiently blocked human VPF, even as their concentrations were lowered. The other antibodies, to peptides 2, 5 and 6, at the relatively high concentration of 0.23 mg/ml, blocked only 21±6, 25±6, and less than 5% of VPF activity, respectively. Also, comparisons of reactivity by antibodies to peptides 1a and 1b against guinea pig and human VPF showed some species preferences. The antibody to peptide 1a (to the guinea pig N-terminus) strongly blocked both human and guinea pig VPF permeability enhancing ability, but blocked guinea pig VPF more effectively than human VPF at a lower concentration. The antibody to peptide 1b (to the human N-terminus) did not block guinea pig VPF permeability (not shown), but completely blocked human VPF.

Experimental Series C

Materials and Methods:

Antibody preparation, labeling with $^{125}$I and biotin

Antibodies were prepared in rabbits against a peptide fragment corresponding to the 25 amino acids comprising the N-terminus of rat VPF except that an amide replaced the carboxyl group at the C-terminus of this peptide fragment. The amino acid sequence of this peptide fragment is: APT-TEGEQKAHEVVKFMDVYQRSYC (SEQ ID NO:31).

Rabbits were immunized at multiple intradermal sites with an emulsion containing 1 mg of rat VPF peptide-keyhold limpet hemocyanin conjugate (Pierce Chemical Co.) in complete Freund's adjuvant; animals were subsequently boosted at 4–6 week intervals with an equivalent amount of the same conjugate in incomplete Freund's adjuvant. Collected serum was stored at −20° C. prior to affinity purification on a column prepared by conjugating 5 mg of peptide to 1 g of CNBr-activated Sepharose (Pharmacia). Typically, 20 ml of antiserum was passed over the column after which the column was washed thoroughly with PBS. Bound antibody was then eluted with 15 ml of 0.1 M acid glycine buffer, pH 2.5. Eluted antibody was immediately diluted in 2 ml of 1 M Tris buffer, pH 8.0, and dialyzed against PBS. Concentrations of affinity-purified antibody were typically 0.5–1.0 mg/ml. Affinity purified antibodies (designated Ab-VPF-N) were prepared from multiple bleeds of three different rabbits; all shared similar properties and were highly specific for mouse VPF/VEGF, as determined by immunoblotting performed as described previously herein.

Antibodies and several different preparations of normal rabbit IgG (hereinafter "nRLgG"; Pierce, Rockford, Ill.) were radioiodinated with $^{125}$I (New England Nuclear, Boston, Mass.) using the IODOGEN method [Lin et al., Cancer Res. 54: 2269–2277 (1994)]. Typically, 0.4 mCI of $^{125}$I was reacted with 1 mg of antibody (0.5 mg/ml). The specific activity of the iodinated product was 0.30–0.35 mCi/mg, and, after the labeled antibodies were affinity-purified, >98% of the radioactivity was perceptible by 10% (w/v) TCA at 4° C. Other preparations of these immunoglobulins were biotinylated for 4–6 h at pH 8.5 at room temperature using a molar ratio of 100:1. Both iodinated and biotinylated antibodies contained only negligible amounts (<3%) of aggregates as determined by HPLC-chromatography on a TSK-GEL G3000SW column (TOSO HAAS, Japan) and retained strong specific reactivity against VPF.

A second anti-VPF antibody, Ab-618, was prepared by immunizing rabbits with recombinant human VPF prepared in a baculovirus system. Preparation of this antibody and its affinity purification have been described [Yeo et al., Cancer Res. 53: 2912–2918 (1993)]. Ab-618 bound and neutralized VPF/VEGF of both human and mouse origin.

Tumor Cells

Three mouse tumors (B16 melanoma, TA3/St mammary carcinoma, and MOT ovarian tumor) were grown in solid form by injecting 2.0–2.5×10$^5$ cells s.c. in 5–7 week old female syngenic mice (C57Bl/6, A/Jax and C3Heb/FeJ, respectively) [20]; tumors (5–40 mg) were harvested at 5–9 days. MOT tumors were also grown in ascites form by injecting 1×10$^6$ tumor cells i.p.

Experiment 6

To demonstrate the characteristics and capabilities of the antibody-radionuclide conjugates in-vivo, distribution studies were performed using tumor-bearing mice. These tumor-bearing mice were injected i.v. by tail vein with 10 μg $^{125}$I-labeled anti-VPF or control antibodies in 200 μl normal saline-0.1% BSA. At various times thereafter (10 min–72 h), the animals were bled from the retro-orbital space, and these sacrificed by $CO_2$ narcosis and exsanguinated. Tumors and a variety of normal tissues were collected, weighted and their radioactivity measured. The vascular volumes of the three tumors and normal control tissues were determined using $^{51}$Cr-radiolabeled RBC as previously reported [Shockley et al., Cancer Res. 52: 357–366 (1992)]. The results are provided by FIGS. 7 and 8 and by Table E3 below.

Figure 7:
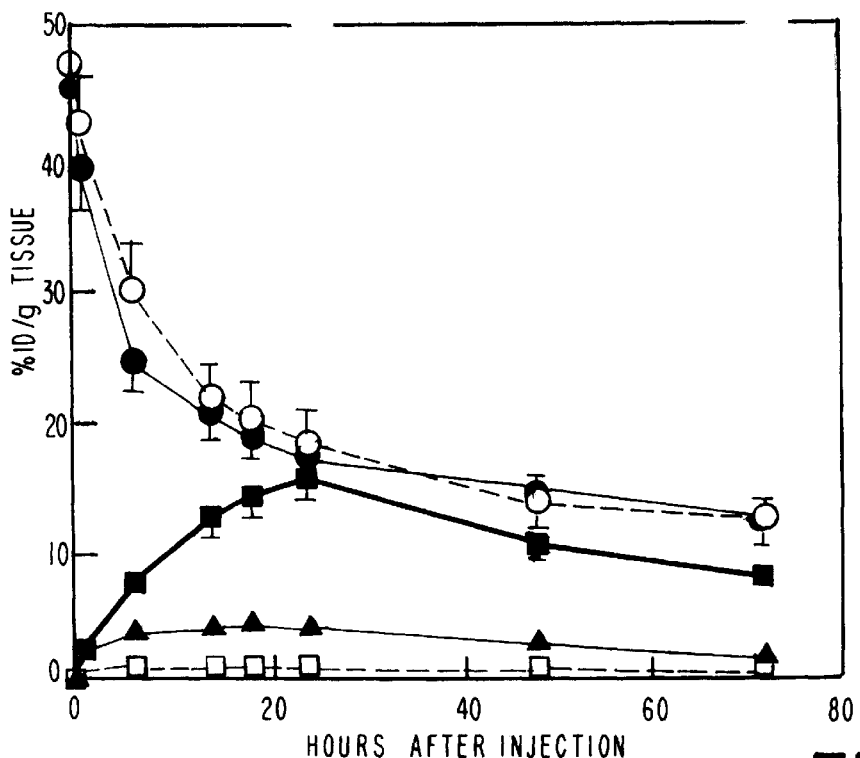
FIG. 7 is a graph showing the distribution of $^{125}$I-labeled Ab-VPF-N and normal rabbit immunoglobulin ($^{125}$I-nRIgG) in live mice bearing solid B16 melanomas, blood, and skeletal muscle.
Figure 8:
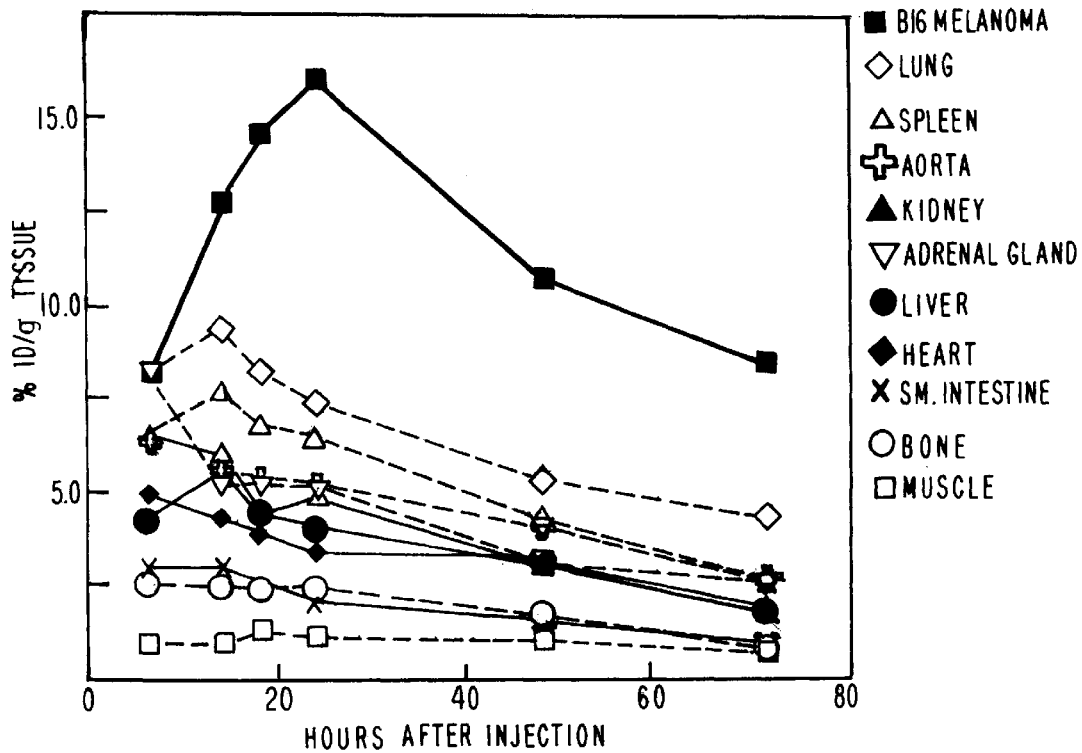
FIG. 8 is a graph showing the distribution of i.v.-injected $^{125}$I-Ab-VPF-N in live mice bearing syngenic B16 melanomas.

The results provided by Table E3 and FIGS. 7–9 respectively are expressed as percentage of injected dose (OD) per gram and weight tissue after correction for radioactivity contributed by the blood space. In some cases, excised tumors were weighed, minced, washed twice with HBSS at 4° C., and the radioactivity present in cell pellets and combined supernatants was measured separately to assess free and cell-bound antibody. Drinking water was supplemented with 0.1% w/v Nal beginning 24 h before injecting radiolabeled antibodies. At least 3 animals (4–6 tumors) were studied at each time point for each antibody. Analysis of variance and statistical analysis were performed using Dunnett's (parametric) or Dunn's (non-parametric) multiple comparison tests, as appropriate.

TABLE E3

| | Tumors/Skeletal Muscle | | | |
| --- | --- | --- | --- | --- |
| | B16 | TA3/St | MOT | Muscle |
| Antibodies: | | | | |
| Ab-VPF-N* | 15.4 ± 1.3 | 16.0 ± 1.0 | 9.2 ± 0.7 | 1.2 |
| nRlgG | 4.3 ± 0.3 | 4.7 ± 0.5 | 3.4 ± 0.4 | 1.2 |
| Ab-618 | — | 2.9 ± 0.1 | 2.5 ± 0.2 | — |
| Ratios: | | | | |
| Ab-VPF-N: tumor/muscle | 12.8 | 13.3 | 7.7 | — |
| tumor: Ab-VPF-N/nRlgG | 3.6 | 3.4 | 2.7 | 1.0 |
| tumor: Ab-VPF-N/Ab-618 | — | 5.5 | 3.7 | — |

*Accumulation of $^{125}$I-Ab-VPF-N in all three mouse tumors was significantly greater than that of either $^{125}$I-nRlgG or $^{125}$I-Ab-618 (p <0.001–<0.0001).

Table E3 shows the accumulation of Ab-VPF-N, Ab-618 and nRIgG in solid mouse tumors 24 hours after i.v. injection of 10 μg of $^{125}$I-labeled protein. Data are expressed as % ID/g tumor. Each datum represents the mean ±SE of 4 to 6 separate tumors.

Also, FIGS. 7–9 respectively reveal the in-vivo distribution of the antibody-radionuclide conjugated molecules.

FIG. 5 shows the distribution of $^{125}$I-labeled Ab VPF-N and control normal rabbit immunoglobin ($^{125}$I-NRIgG) in solid B16 melanomas, blood and skeletal muscle. In this FIG. 7, the data are plotted as percentage of injected dose per g of tissue (% ID/g) versus time (10 min. to 72 h) after i.v. injection of 10 μg radioactive antibody or control immunoglobin. Each data point represents the average of at least 3 animals (±SEM) with either 1 or 2 tumors growing in each mouse. Tumor and skeletal muscle values are corrected for radioactivity contributed by the blood space.

Figure 9B:
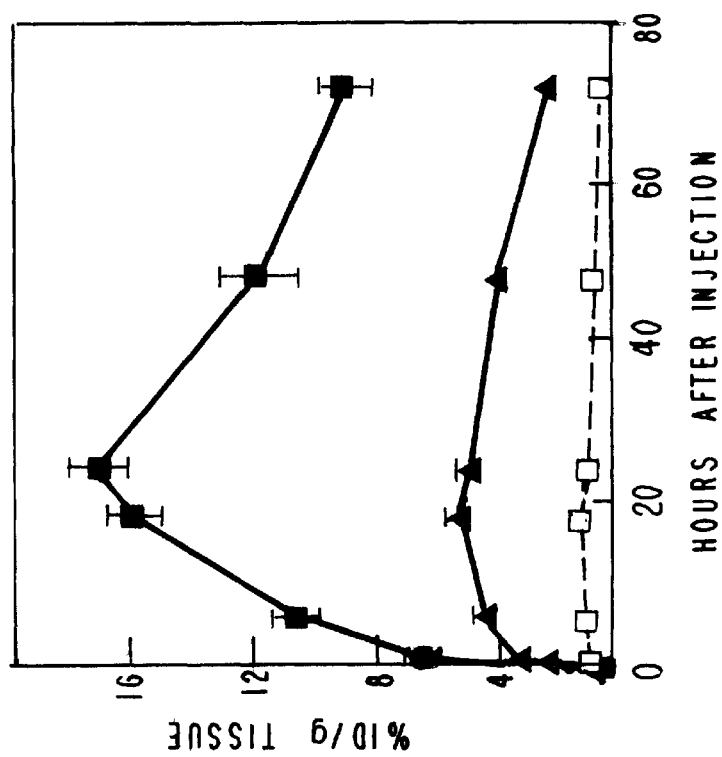
FIGS. 9A and 9B are graphs showing the distribution of $^{125}$I-Ab-VPF-N or $^{125}$I-nRIgG antibodies in solid tumors and in normal skeletal muscle of living animals.
Figure 9A:
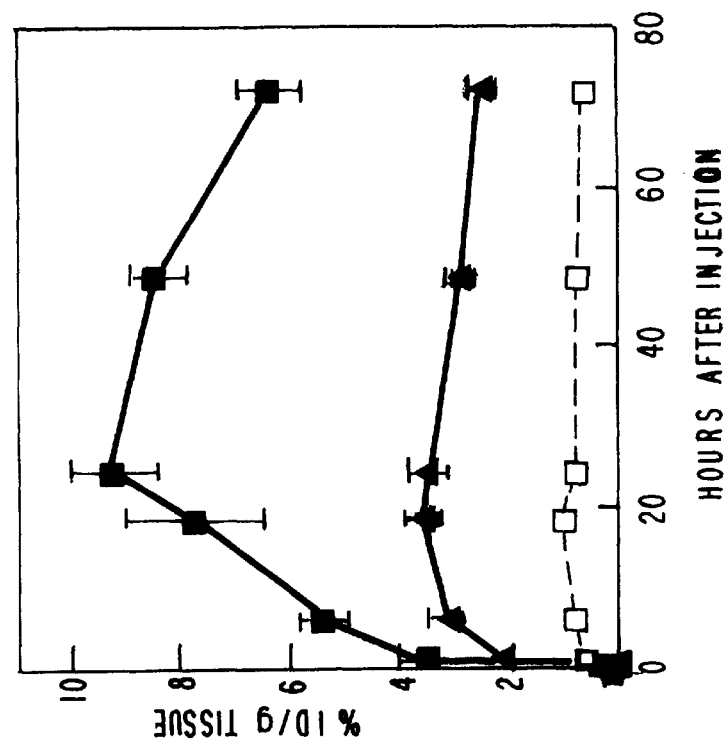

FIG. 8 shows the distribution of i.v.-injected $^{125}$I-Ab-VPF-N in mice bearing syngeric B16 melanomas. The results are self-evident. FIGS. 9A and 9B show the distribution of $^{125}$I-Ab-VPF-N or $^{125}$I-nRIgG in syngereic solid MOT; or TA3/St tumors; and, for comparison, of $^{125}$I-Ab-VPF-N in normal skeletal muscle of the same animals.

Overall Results and Conclusions

Following i.v. injection, $^{125}$I-Ab-VPF-N accumulated in all three tumors to a significantly greater extent than in a variety of normal tissues (FIGS. 7–9). In all three tumors, peak accumulation of Ab-VPF-N occurred at 24 h at concentrations of 9.2–16.0% ID/g (Table E3); thereafter, Ab-VPF-N concentrations in tumors decreased gradually but by less than 50% over the next two days. The lesser maximum accumulation of Ab-VPF-N in MOT as compared with B16 and TA3-St tumors is likely attributable to the relatively lower vascular density of MOT tumors. Thus, these conclusions are drawn.

1. Ab-VPF-N achieved maximal concentrations in normal tissues at earlier times (<18 h) and at substantially lower concentrations than in any of the three tumors. Thus, Ab-VPF-N accumulation was significantly greater ($p<0.001$) in tumors than in skeletal muscle or liver by 6 h and at all subsequent time points; however, differences between tumor and kidney or adrenal gland did not become statistically significant until 14 h and, for lung, until 18 h. At 24 h, differences in Ab-VPF-N accumulation between any of the three tumors and all corresponding normal tissues were highly significant ($p<0.001$); for example, at this interval the concentration of Ab-VPF-N in B16 melanomas exceeded those in different normal tissues by a factor of 2.1 (lung) to 13.3 (skeletal muscle).

2. The specific tissue distribution of Ab-VPF-N was comparable with that of several preparations of normal rabbit IgG (NRIgG) that lacked specificity for VPF. Both Ab VPF-N and nRIgG were cleared from the plasma of B-16 solid tumor-bearing mice with similar kinetics (FIG. 7). Also like Ab-VPF-N, nRIgG accumulated in all three tumors to a greater extent than in skeletal muscle ($p<0.05$ to $p<0.01$ at different time intervals; FIGS. 7 and 9). However, nRIgG achieved much lower peak values in all three tumors (<5% ID/g) than did antibody Ab VPF-N ($p<0.1–0.001$) (Table E3); also, nRIgG reached peak levels earlier, at 18 h versus 24 h for Ab VPF-N. The distribution of nRIgG was virtually identical in the normal tissues of normal control animals and in animals bearing any of the three solid tumors (data not shown).

3. Not all antibodies to VPF accumulated in tumors to an equivalent degree. In particular, when Ab-618 was labeled with $^{125}$I and injected it i.v. into tumor bearing mice, $^{125}$I-Ab-618 did not accumulate in TA3/St or MOT tumors to any greater extent than NRIgG (Table E3).

Thus, in contrast to empirical results with Ab-VPF-N that are directed against only the VPF N-terminus, a polyclonal antibody raised against the whole recombinant VPF protein (Ab-618) did not accumulate selectively in tumors and was distributed in-vivo much as normal rabbit IgG. This result, obtained repeatedly several times, was most surprising in that in-vitro studies with Ab-618 immunoprecipitated both mouse and human VPF from solution and bound VPF in Western blots more effectively than Ab-VPF-N; Ab-618 was also more effective in-vitro than Ab-VPF-N in neutralizing VPF's biological activities. These differences between the in-vivo and in-vitro experiments indicate that once native VPF has bound to blood microvessels, many of its epitopes are no longer spatially accessible to antibody; in comparison, epitopes associated with VPF's N-terminus retained their capacity in-vivo to bind specific antibodies after becoming bound to and associated with microvessel endothelium. It is concluded also that the pool of free VPF present in tumors is relatively small and insufficient to concentrate antibody 618 in amounts that significantly affect its overall tissue distribution as measured by the failure of $^{125}$I-Ab-618 in-vivo to accumulate in tumors in concentrations significantly different from that of $^{125}$I-nRIgG.

Experiment 7

Figure 10:
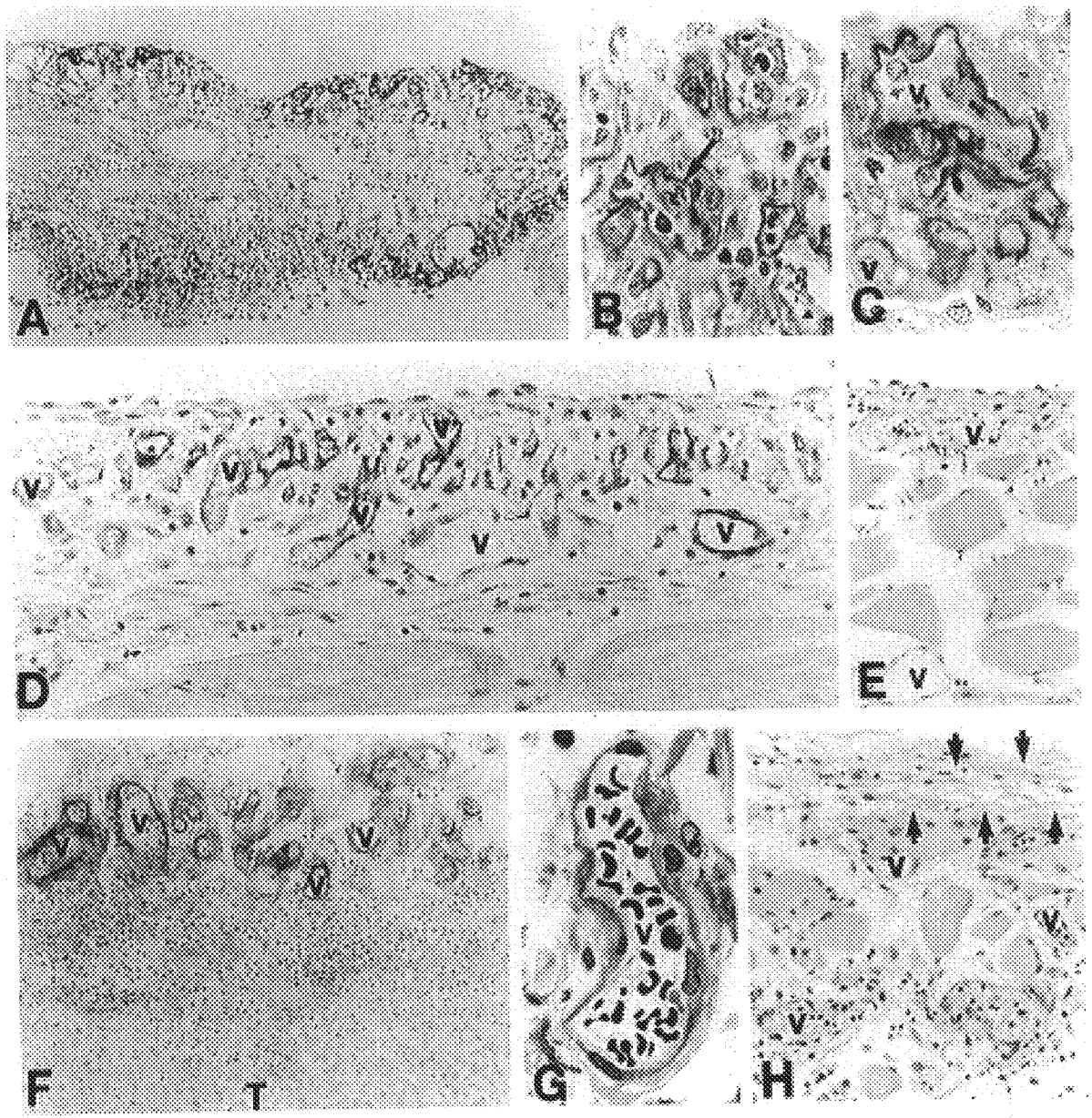
FIGS. 10A–10H are photographs showing avidin-peroxidose staining of syngenic MOT solid (5 day) and ascites (14 day) tumors harvested 24 hours after i.v. injection of 100 µg of bAb-VPF-N or bnRIgG.

Avidin-peroxidase staining for tissue localization of i.v. injected biotinylated antibodies The distribution of biotinylated Ab-VPF-N and control antibodies was followed in solid- or ascites tumor-bearing mice. 100 μg of biotinylated antibodies were injected i.v. in 200 μl of 0.1% BSA-normal saline. Twenty-four hours later, solid tumor-bearing mice were killed and exsanguinated; ascites tumor-bearing mice were harvested similarly but at 5 h because circulating antibodies were cleared rapidly from the plasma into ascites fluid. Solid tumors, peritoneal walls and mesenteries of ascites tumor-bearing mice, and various control tissues were fixed in 3.7% formaldehyde—0.5% glutaraldehyde in 0.1 M phosphate buffered saline, pH 7.6, for 1 h at room temperature and processed for avidin-biotin histochemistry. The results are shown by FIG. 10.

FIGS. 10A–10H show the avidin-peroxidase staining of syngeneic MOT solid (5 day) or ascites (14 day) tumors harvested 24 h after i.v. injection of 100 μg of bAb-VPF-N or bnRLgG. All the figures represent photomicrographs of either 4 μm frozen sections (A, D, E, H) or 1 μm plastic sections (B, C, G) stained with avidin-peroxidase and counterstained with either Mayer's hematoxylin or toluidine blue. FIG. 10A is low-power overview showing intense staining of new, tumor-induced microvessels in mesentery of ascites tumor-bearing animal. FIGS. 10B and 10C show mesenteric microvessels at higher magnification, demonstrating largely abluminal pattern of endothelial cell staining. FIG. 10D shows low-power overview showing intense staining of new, tumor-induced microvessels in peritoneal wall of ascites tumor-bearing mouse. FIG. 10E is a corresponding photomicrograph of peritoneal wall microvessels of MOT ascites tumor bearing mouse injected i.v. with bnRLgG. Note the lack of detectable staining. FIG. 10F shows avidin-peroxidase staining of MOT solid tumor in a mouse injected i.v. with bAb-VPF-N; note intense staining of vessels and weaker staining of matrix at tumor-host interface. FIG. 10G shows a higher magnification view of a labeled vessel in a MOT solid tumor. FIG. 10H shows a solid MOT tumor growing in a mouse injected i.v. with bnRLgG. Vessels are negative but matrix is faintly stained (arrows). v, vessels; T, tumor. Magnifications FIG. 10A, 94×; FIG. 10B 508×; FIG. 10C, 660×; FIG. 10D, 278×; FIGS. 10E, F, 168×; FIG. 10G, 857×; FIG. 10H, 210×.

Localization of i.v. injected biotinylated antibodies in tumor-associated microvessels Biotinylated Ab-VPF-N (bAb-VPF-N) or rRIgG (b-nRLgG) antibodies were injected i.v. into mice bearing either ascites or solid MOT tumors; and were distributed in peritoneal lining tissues of ascites tumor animals, in solid tumors and in two normal tissues (skeletal muscle and liver). These results were determined by avidin-peroxidase histochemistry.

Like solid tumors, ascites tumors elicit a striking angiogenic response such that large numbers of new blood vessels develop in tissues lining the peritoneal cavity. Strong staining for i.v.-injected bAb-VPF-N antibodies was found in microvessels of the mesentery and peritoneal walls of mice bearing MOT ascites tumors (FIGS. 10A–10D). Vessel staining was circumferential and, as determined by 1 μm Epon sections, localized primarily to the abluminal surfaces of individual endothelial cells (FIGS. 10B and 10C); this staining pattern is similar to that demonstrated previously in immunohistochemical experiments when antibodies were applied to tumor sections and localized at either the light or electron microscopic levels. No staining was observed in vessels at a far distance from the tumor-host interface greater than ~0.3 mm. Similar intense staining was observed in tumor-associated microvessels supplying MOT solid tumors (FIGS. 10F and 10G); in addition, tumor stromal matrix immediately surrounding stained vessels was also sometimes stained (FIG. 10F). In contrast, no vessel staining was observed with either ascites or solid MOT tumors in mice injected i.v. with b-nRIgG (FIGS. 10E and 10H), although faint stromal staining was sometimes observed focally (FIG. 10H).

Conclusion

Previous immunohistochemical studies performed on fixed and processed sections of these and other tumors had demonstrated that the Ab-VPF-N stained VPF/VEGF that was bound to tumor-associated blood microvessels and particularly the abluminal surface of tumor microvascular endothelium. This experiment has now extended these findings, demonstrating that these antibodies, when biotinylated and administered intravenously, have access to tumor microvascular endothelium-associated VPF in living animals. Moreover, the concentrations of Ab-VPF-N achieved in the three different solid tumors we studied were proportional to overall tumor vascularity: B16=TA3/St>>MOT [24]. These findings therefore demonstrate the feasibility of using antibodies directed against the different regions of VPF as a delivery vehicle for selectively targeting the microvasculature of solid and ascites tumors. bAb-VPF-N also concentrated in microvessels lining the peritoneal cavities of ascites tumor-bearing mice where VPF had also been demonstrated previously by immunohistochemistry.

The present invention is not to be restricted in scope nor limited in form except by the claims appended hereto.

What we claim:

1. A mixed immunological preparation for concurrent specific binding to multiple epitopes presented by spatially exposed regions of immobilized vascular permeability factor (VPF) bound in-vivo to endothelial cells of a tumor-associated blood vessel, said immunological preparation comprising not less than two types of conjugate molecules in admixture, (a) wherein a first type of conjugate molecule comprises
at least the binding portion of a first antibody which binds specifically to an epitope presented by a spatially exposed region of VPF bound to a tumor associated blood vessel in-vivo, and
a single type of effector moiety covalently bound to said first antibody; and (b) wherein a second type of conjugate molecule comprises
at least the binding portion of a second antibody which binds specifically to another epitope presented by a spatially exposed region of VPF bound to a tumor-associated blood vessel in-vivo, and
said single type of effector moiety covalently bound to said second antibody.

2. A mixed immunological preparation for concurrent specific binding to a single epitope presented by a spatially exposed region of immobilized vascular permeability factor (VPF) bound in-vivo to endothelial cells of a tumor-associated blood vessel, said immunological preparation comprising not less than two types of conjugate molecules in admixture, (a) wherein a first type of conjugate molecule comprises
at least the binding portion of a single type of antibody which binds specifically to an epitope presented by a spatially exposed region of immobilized VPF bound to a tumor-associated blood vessel in-vivo, and
a first type of effector moiety covalently bound to said single type of antibody; and (b) wherein a second type of conjugate molecule comprises
at least the binding portion of said single type of antibody which binds specifically to said epitope presented by a spatially exposed region of immobilized VPF bound to a tumor-associated blood vessel in-vivo, and
a second type of effector moiety covalently bound to said single type of antibody.

3. A mixed immunological preparation for concurrent specific binding to multiple epitopes presented by spatially exposed regions of immobilized vascular permeability factor (VPF) bound in-vivo to endothelial cells of a tumor-associated blood vessel, said immunological preparation comprising not less than two types of conjugate molecules in admixture, (a) wherein a first type of conjugate molecule comprises
at least the binding portion of an first antibody which binds specifically to an epitope presented by a spatially exposed region of immobilized VPF bound to a tumor-associated blood vessel in-vivo, and
a first type of effector moiety covalently bound to said first antibody; and (b) wherein a second type of conjugate molecule comprises
at least the binding portion of a second antibody which binds specifically to another epitope presented by a spatially exposed region of immobilized VPF bound to a tumor-associated blood vessel in-vivo, and
a second type of effector moiety covalently bound to said second antibody.

4. The immunological preparation as recited in claim 1, 2, or 3 wherein said binding portion of a conjugate molecule is selected from the group consisting of a whole antibody, and $F(ab')_2$ fragment, and a Fab fragment.

5. The immunological preparation as recited in claim 1, 2, or 3 wherein said effector moiety of a conjugate molecule is selected from the group consisting of radionuclides, antimetabolites, heavy metals, enzymes, bacterial exotoxins, and active complexes.

* * * * *

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
      (A) LENGTH: 147 amino acids
      (B) TYPE: amino acid
      (C) STRANDEDNESS: single
      (D) TOPOLOGY: linear (xi) SEQUENCE DESCRIPTION: SEQ ID NO:1:

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125
```

```
Glu Cys Arg Pro Lys Lys Asp Arg Ala Arg Gln Glu Lys Cys Asp Lys
            130                 135                 140

Pro Arg Arg
145
```

(2) INFORMATION FOR SEQ ID NO:2:

(i) SEQUENCE CHARACTERISTICS:
        (A) LENGTH: 191 amino acids
        (B) TYPE: amino acid
        (C) STRANDEDNESS: single
        (D) TOPOLOGY: linear (xi) SEQUENCE DESCRIPTION: SEQ ID NO:2:

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Asn Pro Cys Gly
            130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190
```

(2) INFORMATION FOR SEQ ID NO:3:

(i) SEQUENCE CHARACTERISTICS:
        (A) LENGTH: 215 amino acids
        (B) TYPE: amino acid
        (C) STRANDEDNESS: single
        (D) TOPOLOGY: linear (xi) SEQUENCE DESCRIPTION: SEQ ID NO:3:

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80
```

```
Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
130                 135                 140

Arg Gly Lys Gly Arg Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
            195                 200                 205

Arg Cys Asp Lys Pro Arg Arg
            210             215

(2) INFORMATION FOR SEQ ID NO:4:

(i) SEQUENCE CHARACTERISTICS:
        (A) LENGTH: 232 amino acids
        (B) TYPE: amino acid
        (C) STRANDEDNESS: single
        (D) TOPOLOGY: linear (xi) SEQUENCE DESCRIPTION: SEQ ID NO:4:

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
130                 135                 140

Arg Gly Lys Gly Arg Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
            195                 200                 205
```

```
Thr Asp Ser Arg Cys Lys Ala Arg Gln Leu Glu Leu Asn Glu Arg Thr
    210                 215                 220

Cys Arg Cys Asp Lys Pro Arg Arg
225                 230
```

(2) INFORMATION FOR SEQ ID NO:5:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO:5:

```
Ala Pro Met Ala Glu Gly Gly Gly Gln Asn His His Glu Val Val Lys
1               5                   10                  15

Phe Met Asp Val Tyr Gln Arg Ser Tyr Cys
            20                  25
```

(2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:6:

```
Cys Glu Cys Arg Pro Lys Lys Asp Arg Ala Arg Gln Glu Lys Lys Ser
1               5                   10                  15

Val Arg
```

(2) INFORMATION FOR SEQ ID NO:7:

(i) SEQUENCE CHARACTERISTICS:
        (A) LENGTH: 19 amino acids
        (B) TYPE: amino acid
        (C) STRANDEDNESS: single
        (D) TOPOLOGY: linear (xi) SEQUENCE DESCRIPTION: SEQ ID NO:7:

```
Lys Ala Arg Gln Leu Glu Leu Asn Glu Arg Thr Cys Arg Cys Asp Lys
1               5                   10                  15

Pro Arg Arg
```

(2) INFORMATION FOR SEQ ID NO:8:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO:8:

```
Ala Pro Met Ala Glu Gly Gly Gly Gln Asn His His Glu Val Val Lys
1               5                   10                  15

Phe Met Asp Val Tyr Gln Arg Ser Tyr Cys
            20                  25
```

(2) INFORMATION FOR SEQ ID NO:9:

(i) SEQUENCE CHARACTERISTICS:
        (A) LENGTH: 14 amino acids
        (B) TYPE: amino acid

```
            (C) STRANDEDNESS: single
            (D) TOPOLOGY: linear (xi) SEQUENCE DESCRIPTION: SEQ ID NO:9:

Cys Glu Cys Arg Pro Lys Lys Asp Arg Ala Arg Gln Glu Lys
1               5                   10

(2) INFORMATION FOR SEQ ID NO:10:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO:10:

Cys Asp Lys Pro Arg Arg
1               5

(2) INFORMATION FOR SEQ ID NO:11:

(i) SEQUENCE CHARACTERISTICS:
            (A) LENGTH: 26 amino acids
            (B) TYPE: amino acid
            (C) STRANDEDNESS: single
            (D) TOPOLOGY: linear (xi) SEQUENCE DESCRIPTION: SEQ ID NO:11:

Ala Pro Met Ala Glu Gly Gly Gly Gln Asn His His Glu Val Val Lys
1               5                   10                  15

Phe Met Asp Val Tyr Gln Arg Ser Tyr Cys
            20                  25

(2) INFORMATION FOR SEQ ID NO:12:

(i) SEQUENCE CHARACTERISTICS:
            (A) LENGTH: 14 amino acids
            (B) TYPE: amino acid
            (C) STRANDEDNESS: single
            (D) TOPOLOGY: linear (xi) SEQUENCE DESCRIPTION: SEQ ID NO:12:

Cys Glu Cys Arg Pro Lys Lys Asp Arg Ala Arg Gln Glu Asn
1               5                   10

(2) INFORMATION FOR SEQ ID NO:13:

(i) SEQUENCE CHARACTERISTICS:
            (A) LENGTH: 19 amino acids
            (B) TYPE: amino acid
            (C) STRANDEDNESS: single
            (D) TOPOLOGY: linear (xi) SEQUENCE DESCRIPTION: SEQ ID NO:13:

Lys Ala Arg Gln Leu Glu Leu Asn Glu Arg Thr Cys Arg Cys Asp Lys
1               5                   10                  15

Pro Arg Arg (2) INFORMATION FOR SEQ ID NO:14:

(i) SEQUENCE CHARACTERISTICS:
            (A) LENGTH: 26 amino acids
            (B) TYPE: amino acid
            (C) STRANDEDNESS: single
            (D) TOPOLOGY: linear
```

(xi) SEQUENCE DESCRIPTION: SEQ ID NO:14:

Ala Pro Met Ala Glu Gly Gly Gly Gln Asn His His Glu Val Val Lys
1               5                   10                  15

Phe Met Asp Val Tyr Gln Arg Ser Tyr Cys
            20                  25

(2) INFORMATION FOR SEQ ID NO:15:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:15:

Cys Glu Cys Arg Pro Lys Lys Asp Arg Ala Arg Gln Glu Lys Lys Ser
1               5                   10                  15

Val Arg (2) INFORMATION FOR SEQ ID NO:16:

(i) SEQUENCE CHARACTERISTICS:
        (A) LENGTH: 19 amino acids
        (B) TYPE: amino acid
        (C) STRANDEDNESS: single
        (D) TOPOLOGY: linear (xi) SEQUENCE DESCRIPTION: SEQ ID NO:16:

Lys Ala Arg Gln Leu Glu Leu Asn Glu Arg Thr Cys Arg Cys Asp Lys
1               5                   10                  15

Pro Arg Arg (2) INFORMATION FOR SEQ ID NO:17:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (v) FRAGMENT TYPE:  N-terminal (xi) SEQUENCE DESCRIPTION: SEQ ID NO:17:

Ala Pro Met Ala Glu Gly Glu Gln Lys Pro Arg Glu Val Val Lys Phe
1               5                   10                  15

Met Asp Val Tyr Lys Arg Ser Tyr Cys
            20                  25

(2) INFORMATION FOR SEQ ID NO:18:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (v) FRAGMENT TYPE:  N-terminal (xi) SEQUENCE DESCRIPTION: SEQ ID NO:18:

Ala Pro Met Ala Glu Gly Gly Gly Gln Asn His His Glu Val Val Lys
1               5                   10                  15

-continued

```
Phe Met Asp Val Tyr Gln Arg Ser Tyr Cys
            20                  25

(2) INFORMATION FOR SEQ ID NO:19:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (v) FRAGMENT TYPE:  internal (xi) SEQUENCE DESCRIPTION: SEQ ID NO:19:

Cys Gly Cys Arg Pro Lys Lys Asp Arg Ala Arg Gln Glu Lys Lys Ser
1               5                   10                  15

Val Thr (2) INFORMATION FOR SEQ ID NO:20:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (v) FRAGMENT TYPE:  N-terminal (xi) SEQUENCE DESCRIPTION: SEQ ID NO:20:

Ala Pro Met Ala Glu Gly Glu Gln Lys Pro Arg Glu Val Val Lys Phe
1               5                   10                  15

Met Asp Val Tyr Lys Arg Ser Tyr Cys
            20                  25

(2) INFORMATION FOR SEQ ID NO:21:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (v) FRAGMENT TYPE:  N-terminal (xi) SEQUENCE DESCRIPTION: SEQ ID NO:21:

Ala Pro Met Ala Glu Gly Gly Gly Gln Asn His His Glu Val Val Lys
1               5                   10                  15

Phe Met Asp Val Tyr Gln Arg Ser Tyr Cys
            20                  25

(2) INFORMATION FOR SEQ ID NO:22:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (v) FRAGMENT TYPE:  internal
```

(xi) SEQUENCE DESCRIPTION: SEQ ID NO:22:

His Pro Ile Glu Thr Leu Val Asp Ile Phe Gln Glu Tyr Pro Asp Glu
1               5                   10                  15

Ile Glu Tyr Leu Phe Lys
            20

(2) INFORMATION FOR SEQ ID NO:23:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (v) FRAGMENT TYPE:  internal (xi) SEQUENCE DESCRIPTION: SEQ ID NO:23:

Pro Ser Cys Val Pro Leu Met Arg Cys Gly Gly Cys Cys Asn Asp Glu
1               5                   10                  15

Gly (2) INFORMATION FOR SEQ ID NO:24:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (v) FRAGMENT TYPE:  internal (xi) SEQUENCE DESCRIPTION: SEQ ID NO:24:

Leu Gln Cys Val Pro Thr Glu Glu Ser Asn Ile Thr Met Gln Ile Met
1               5                   10                  15

Arg Ile Lys (2) INFORMATION FOR SEQ ID NO:25:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (v) FRAGMENT TYPE:  internal (xi) SEQUENCE DESCRIPTION: SEQ ID NO:25:

Pro His Gln Gly Gln His Ile Gly Glu Met Ser Phe Leu Gln His Asn
1               5                   10                  15

Lys (2) INFORMATION FOR SEQ ID NO:26:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:26:

```
Cys Glu Cys Arg Pro Lys Lys Asp Arg Ala Arg Gln Glu Lys Lys Ser
1               5                  10                  15
Val Arg
```

(2) INFORMATION FOR SEQ ID NO:27:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:27:

```
Gly Lys Gly Lys Gly Gln Lys Arg Lys Arg Lys Lys Ser Arg Tyr Lys
1               5                  10                  15
Ser Trp Ser Val Pro Cys
            20
```

(2) INFORMATION FOR SEQ ID NO:28:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:28:

```
Gly Pro Cys Ser Glu Arg Arg Lys His Leu Phe Val Gln Asp Pro Gln
1               5                  10                  15
Thr Cys
```

(2) INFORMATION FOR SEQ ID NO:29:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:29:

```
Gln Thr Cys Lys Cys Ser Cys Lys Asn Thr Asp Ser Arg Cys Lys Ala
1               5                  10                  15
Arg
```

(2) INFORMATION FOR SEQ ID NO:30:

(i) SEQUENCE CHARACTERISTICS:
        (A) LENGTH: 19 amino acids
        (B) TYPE: amino acid
        (C) STRANDEDNESS: single
        (D) TOPOLOGY: linear -continued

```
    (ii) MOLECULE TYPE: peptide (v) FRAGMENT TYPE:  internal (xi) SEQUENCE DESCRIPTION: SEQ ID NO:30:

Lys Ala Arg Gln Leu Glu Leu Asn Glu Arg Thr Cys Arg Cys Asp Lys
1               5                   10                  15

Pro Arg Arg (2) INFORMATION FOR SEQ ID NO:31:

(i) SEQUENCE CHARACTERISTICS:
          (A) LENGTH: 25 amino acids
          (B) TYPE: amino acid
          (C) STRANDEDNESS: single
          (D) TOPOLOGY: linear (ii) MOLECULE TYPE: peptide (v) FRAGMENT TYPE:  N-terminal (xi) SEQUENCE DESCRIPTION: SEQ ID NO:31:

Ala Pro Thr Thr Glu Gly Glu Gln Lys Ala His Glu Val Val Lys Phe
1               5                   10                  15

Met Asp Val Tyr Gln Arg Ser Tyr Cys
            20                  25
```